US 6,572,751 B1

United States Patent
De Boer et al.

(10) Patent No.: US 6,572,751 B1
(45) Date of Patent: Jun. 3, 2003

(54) METHOD AND APPARATUS FOR CONTINUOUS FLOW ISOELECTRIC FOCUSING FOR PURIFYING BIOLOGICAL SUBSTANCES

(75) Inventors: Gerben Foppe De Boer, Lelystad (NL); Oto Sova, Kosice (SK)

(73) Assignee: Cerberus Enterprises B.V., Lelystad (NL)

( * ) Notice: Subject to any disclaimer, the term of this patent is extended or adjusted under 35 U.S.C. 154(b) by 0 days.

(21) Appl. No.: 09/377,868

(22) Filed: Aug. 20, 1999

Related U.S. Application Data

(63) Continuation-in-part of application No. PCT/NL98/00104, filed on Feb. 20, 1998.

(30) Foreign Application Priority Data

Feb. 20, 1997 (EP) ............................................. 97200489

(51) Int. Cl.[7] ........................ G01N 27/26; G01N 27/447
(52) U.S. Cl. ....................... 204/548; 204/644; 204/450; 204/600
(58) Field of Search ................................ 204/548, 600, 204/644, 450

(56) References Cited

U.S. PATENT DOCUMENTS 4,833,074 A * 5/1989 Fagerhol et al. ............... 435/7
5,238,836 A * 8/1993 Certa et al. ............... 435/252.3
6,127,151 A * 10/2000 Novotny et al. ........... 435/71.1

* cited by examiner

Primary Examiner—Jill Warden
Assistant Examiner—John S. Starsiak, Jr.
(74) Attorney, Agent, or Firm—Browdy and Neimark, PLLC

(57) ABSTRACT

The invention provides a continuous flow apparatus and method for purifying charged substances from solutions or suspensions by isoelectric focusing on an industrial scale.

The apparatus comprises a separating chamber, a pair of vertical electrodes (9) located at the extremes of the apparatus, an anion- or a cation-selective membrane (10) located near each of the electrodes (9) for separating electrode spaces from a central part of the apparatus, one or more outflow ports (12) for separating liquid fractions at the upper part of the chamber, two secondary outflow ports (11) being provided in the upper part of each of the electrode spaces, one or more vertical wall(s) (6) between each of said outflow ports partitioning the chamber at least at the height of said outflow ports (11,12), and a plurality of vertical permeable partition walls (13) to enable a convection-free upward flow.

The apparatus invention does not require additional amphoteric buffering solutions to establish a suitable pH gradient, and can be used for purification of polynucleotides, amino acids, peptides, proteins, organic solvents and beverages.

11 Claims, 11 Drawing Sheets

13

13

Fig 8a
Fig 8b
Fig 8c
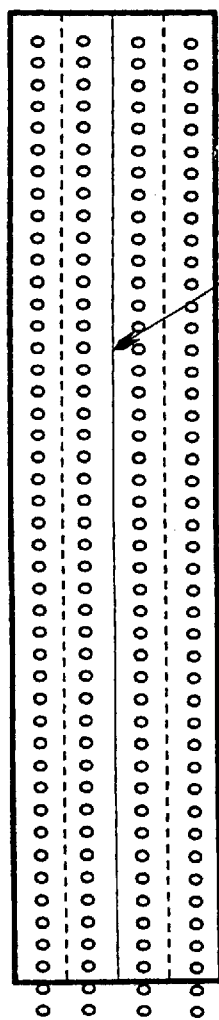
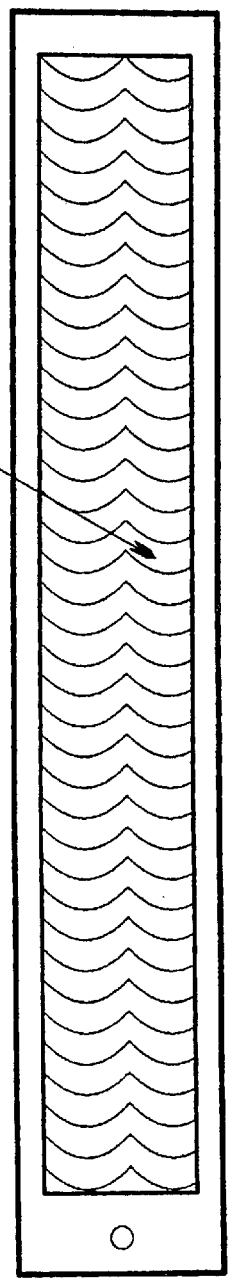
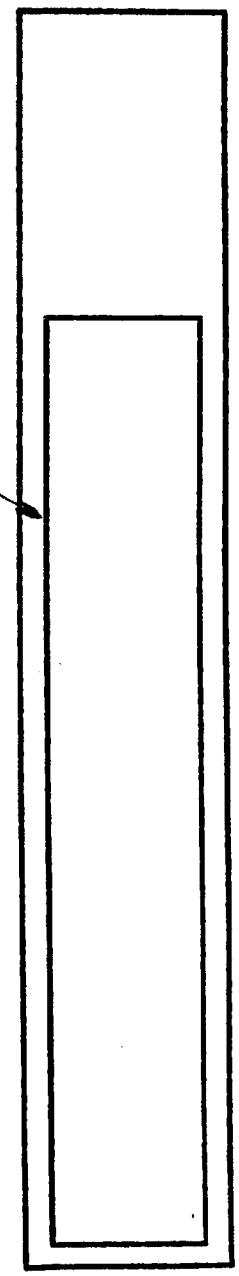

METHOD AND APPARATUS FOR CONTINUOUS FLOW ISOELECTRIC FOCUSING FOR PURIFYING BIOLOGICAL SUBSTANCES

CROSS-REFERENCE TO RELATED APPLICATIONS

This application is a continuation-in-part of PCT/NL98/00104, filed Feb. 20, 1998, the entire contents of which are incorporated by reference.

BACKGROUND OF THE INVENTION

1. Field of the Invention

The present invention relates to purification, isolation, concentration and separation of organic or biological substances by a novel continuous flow isoelectric focusing method (contifocusing) and apparatus (contifocuser), a technique which employs an electrically low-conductive field for concentration or separation of charged substances. Centrifugation, filtration, absorption steps or carrier electrolyte or ampholyte buffers, to establish suitable pH gradients, are not used.

2. Description of the Related Art

Isoelectric focusing is a known technique for separating charged molecules such as proteins from a mixture containing them, using the principle that such charged amphoteric molecules have a zero net charge at a particular pH, the so-called isoelectric point (pI value). The compounds will migrate to the pH of their own isoelectric point if they are subjected to an electric field, and are separated accordingly.

Methods and apparatus for static isoelectric focusing are known, e.g. from WO 79/00942; EP-A-256552 and U.S. Pat. No. 5,256,269. A shortcoming of this type of arrangement is the small quantity to be purified, and its collection in a batch-wise operation. The technological background of the present invention is described in a continuous flow electrophoresis apparatus in U.S. Pat. No. 4,465,582 (1982) which employs a controlled fluid flow in the electrode chambers, which flow is running parallel but separate from the flow in the "working" chambers. U.S. Pat. No. 5,160,594 discloses an isoelectrofocusing apparatus having a forced recirculation in every cell, i.e. a recycling isoelectric focusing process. Recycling is not used in the present invention. The US patent employs a plurality of devices for preventing mixing of semi-purified and crude amphoteric substances. Additional cooling is required in every cell to reduce ohmic heating. Strong acids and bases, a catholyte or anolyte, are confined to the electrode chambers by ion-selective membranes to repel the negatively or positively charged ions and to establish suitable pH gradients. As opposed to U.S. Pat. No. 5,160,594, the present invention uses ion-selective membranes for different purposes, namely to selectively permit passing of low-molecular substances towards the electrode space for discarding from the electrode outflow port. All prior art devices require carrier ampholytes for the working chambers, which have a relatively low conductivity and a buffering capacity. U.S. Pat. No. 5,160,594 describes a maximum conductivity up to 600 $\mu$S/cm, which is far less than the conductivity up to 5000 $\mu$S/cm of the present invention. Like other prior art apparatus it is not designed for purification on an industrial scale and, in addition, U.S. Pat. No. 5,160,594 does not provide examples of substances to be purified.

A continuous flow isoelectric focusing method and apparatus, without using carrier ampholyte buffers but for use on an industrial scale, are disclosed in Hungarian patent 210,584 (1992). It describes an upward flow system through the chambers by gravitation into the separation chambers up to the level of the outflow port. The system includes two non-conductive solution chambers where the second is having two or more solution outflow ports and a passageway for a downwards flow of the solution from the first chamber into the bottom of the second chamber. A pair of electrodes are located in the second chamber. A plurality of adjacent partition members are located in the second chamber and extended there across in order to provide substantially convection-free solution and current flow pathways in the horizontal direction. A shortcoming of HU 210,584 is the fact that in the inflow solution chamber a gradient can be formed by itself. The inflow of the solution by dropping is difficult to control. The upward flow system of the Hungarian patent is less vulnerable to intrinsic gradient formation, alike in the present invention, but the two-chamber system is complicated and difficult to construct. In addition, separation of organic solutions occurs at both opposite sides of the second separating chamber close to the electrodes. Inorganic ions are easily mixing with the single fractions of inorganic or biological substances to be separated. A second separation step is frequently required.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a contifocuser for separating substances in an electrically conductive solution, which apparatus is made from electrically non-conductive material and includes a brick-form separating chamber having one liquid inflow, two electrode space outflows and one or more working solution outflow ports and a passageway for upward flow of the solution from the bottom up to top outflows. The ratio of the height, the width and the depth of the separation chamber can be e.g. 3:2:0.2. A pair of electrodes are located in vertical position along both opposite most narrow walls of the separating chamber. They are adapted to be coupled to an external direct current (DC) power supply.

The apparatus is divided into three parts by two partitions made from ion-selective membranes. These ion-selective membrane partitions are situated in vertical position at both sides of the apparatus near the electrodes, so that they each separate about $\frac{1}{25}$ to $\frac{1}{15}$ parts from both ends. Both vertical ion-selective partitions have an opening at the bottom with a diameter of one half of the inflow pipe of the apparatus. In particular, the one enclosing the cathode space is a cation-selective membrane and the other is an anion-selective membrane. The ion-selective membranes have a specificity chosen to permit the transfer of either cations or anions in order to be eliminated in the waste outflow ports. At both ends, the waste outflow openings are located near the electrodes at $\frac{1}{40}$ to $\frac{1}{10}$ from the top rim of the apparatus. The working outflows, for collecting the substances to be purified, are situated at the same level in the middle. Advantageously, the contifocuser comprises at least three of said outflow ports. Between the outflow ports, except in the electrodes spaces, are dividing vertical partitions made from electrically non-conductive material, closed in their upper quarter and with small openings from bottom up to e.g. three quarters of their height.

As a further improvement, a plurality of adjacent alternating zigzag-shaped or U-shaped or multiple U form partition members may be located in the remaining space of the apparatus between the above-mentioned partitions, but not in the electrode spaces. These are also made of electrically non-conductive material and are perforated or made from porous material permeable for ions and molecules in both directions, and extend from the bottom up to the lowest level of the working outflow port and across the chamber. The partition members are placed freely over the entire width of the apparatus, and are the novel means to provide a substantially convection-free solution but provide an undisturbed flow of electrolytes or amphoteric particles in the horizontal direction. The perforated membranes are in a spaced-apart relationship in order to provide an undisturbed vertical flow. This invention has important advantages over prior art devices in that it can process up to 3,600 L/day of earthworm enzymes (prior art according to HU 210,584: 280–300 L) producing 80,000–170,000 U. of purified enzyme per L/day (HU 210,584: 60,000–70,000 U.).

Another advantage of this invention is that the solution or suspension may have a conductivity in the range of 50–5000 $\mu$S/cm, instead of 50–2000 $\mu$S/cm of the prior art devices (U.S. Pat. No. 5,160,594 describes in the tables a conductivity up to 600 $\mu$S/cm). In this invention, the solution flows through a chemically inert passageway of said apparatus, vertically upwards through a plurality of vertical flow paths formed between the two vertical ion-permeable membrane partitions which separate the spaced electrodes from the working space in-between. A small part of the solution flows horizontally through small openings in these partitions. A bias voltage is applied between the electrodes which results in a separation of the electrically charged components in horizontal direction across the apparatus towards the cathode or the anode. The components are collected as they exit through the outflow ports located near the upper part of the apparatus. The small and low M.W., and charged components, i.e. metals and ions, move to the electrode spaces. They exit the apparatus through waste outflow ports, and are therewith separated from the higher M.W. substances which move to the centre of the apparatus.

In this invention, the target substance comprises at least one zwitterionic species characterised by a pI value, wherein said species is surrounded by amphoteric impurities. A pH gradient is formed across the apparatus by said impurities when the bias potential is applied. In the pH gradient, the zwitterionic species are driven to a point with a pH corresponding to the pI of said species, and is neutralised. Thereafter, the substance flows in the vertical direction to an outflow port in the upper part of the apparatus.

In order to increase the capacity, two contifocusers can be attached to each other in a twin configuration, and are separated by a waterproof vertical cross-wall (17). The "twin-focuser" has common electrode spaces (2) at both ends of the apparatus, and one pair of electrodes serves for both contifocusing chambers. The twin-focuser has a common inflow port (7) in the centre-bottom of the apparatus where the incoming flow is equally divided between both contifocusers. From both electrode spaces one or two electrode outflows can be arranged (11). Twin-focuser has at both sides working outflow ports (12) as in the original contifocuser. The twin-focuser has a double flow rate and double separation capacity whilst the electrical energy requirement is increased by one-third only.

Purification, isolation, and concentration of biological substances on an industrial scale is described. Centrifugation, filtration, absorption steps or additional carrier ampholyte buffers to establish suitable pH gradients, are not necessary. Multiple dividing and perforated partition members, permeable for particles in both directions, are placed vertically over the entire width of the apparatus as the novel means to provide a substantially convection-free solution, and to create an undisturbed vertical fluid flow.

The contifocuser is designed for cost-effective purification of e.g., plasmids, peptides, amino acids, enzymes, immunoglobulins, antigens for diagnostic testkits which are manufactured by combining/mixing with further testkit components, or for preparing viral or bacterial (subunit) vaccines which are manufactured by combining/mixing with further vaccine components, allergens, and for isolating cell populations or milk-, blood-, or urine-borne recombinant products. The contifocuser can further be used for elimination of impurities or toxic substances from yeast or bacterial fermentation processes, antibiotics, organic solvents, drinking water and beverages.

The contifocuser can also be used for isolating or purifying products which are expressed by or extracted from a microorganism (including bacteria, fungi, yeasts, algae and other mono- or oligocellular organisms), animals (including mammals, insects, invertebrates) or plants (including seaweeds, plankton, mushrooms, mosses, herbs and higher plants), or parts or derivatives thereof. Such products include microbial expression products, substances produced by transgenic mammals such as cows and pigs producing medicinal products in their milk, and substances extracted from forestry and plantation products. Examples are natural colours, pesticides, lignin, polyols such as xylitol, carbohydrates, oligo- and polysaccharides such as xylans and microcrystalline cellulose, dietary and other fibres, glycoproteins, and lipoproteins.

Most of the biological substances separated or purified by the apparatus and method according to the present invention are amphoteric substances, although the apparatus is not limited to separating or purifying amphoteric substances and can include ions, heavy metals, etc.

The present invention also provides a hydrolytic enzyme or mixture of enzymes purified using the apparatus of the present invention and methods for using such a purified hydrolytic enzyme or enzyme mixture.

BRIEF DESCRIPTION OF THE DRAWINGS

FIGS. 8A–8C are side views of the three types of space partitions of the apparatus.

DETAILED DESCRIPTION OF PREFERRED EMBODIMENTS

Figure 1:
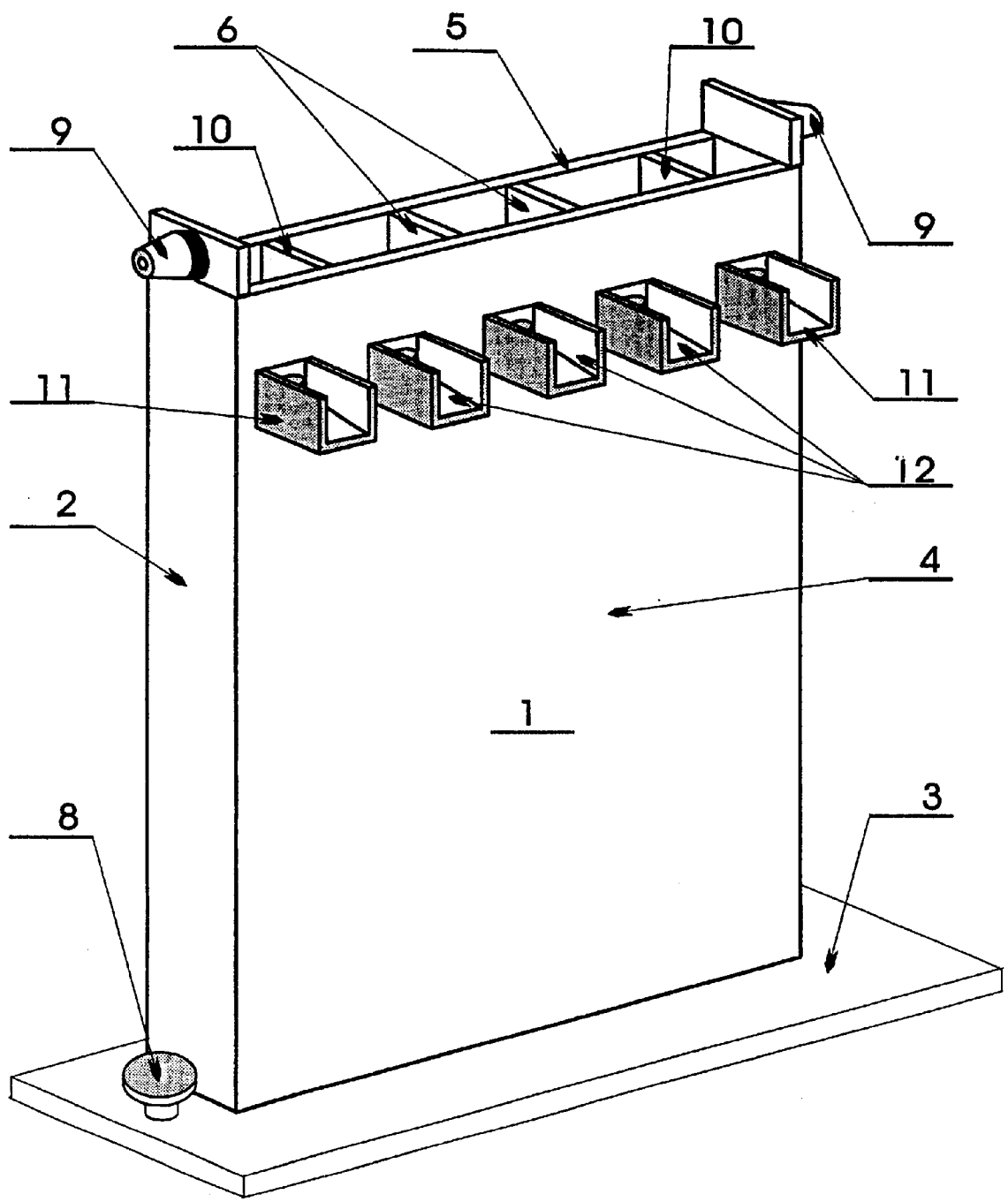
FIG. 1 is a perspective view of the apparatus of the invention.
Figure 2:
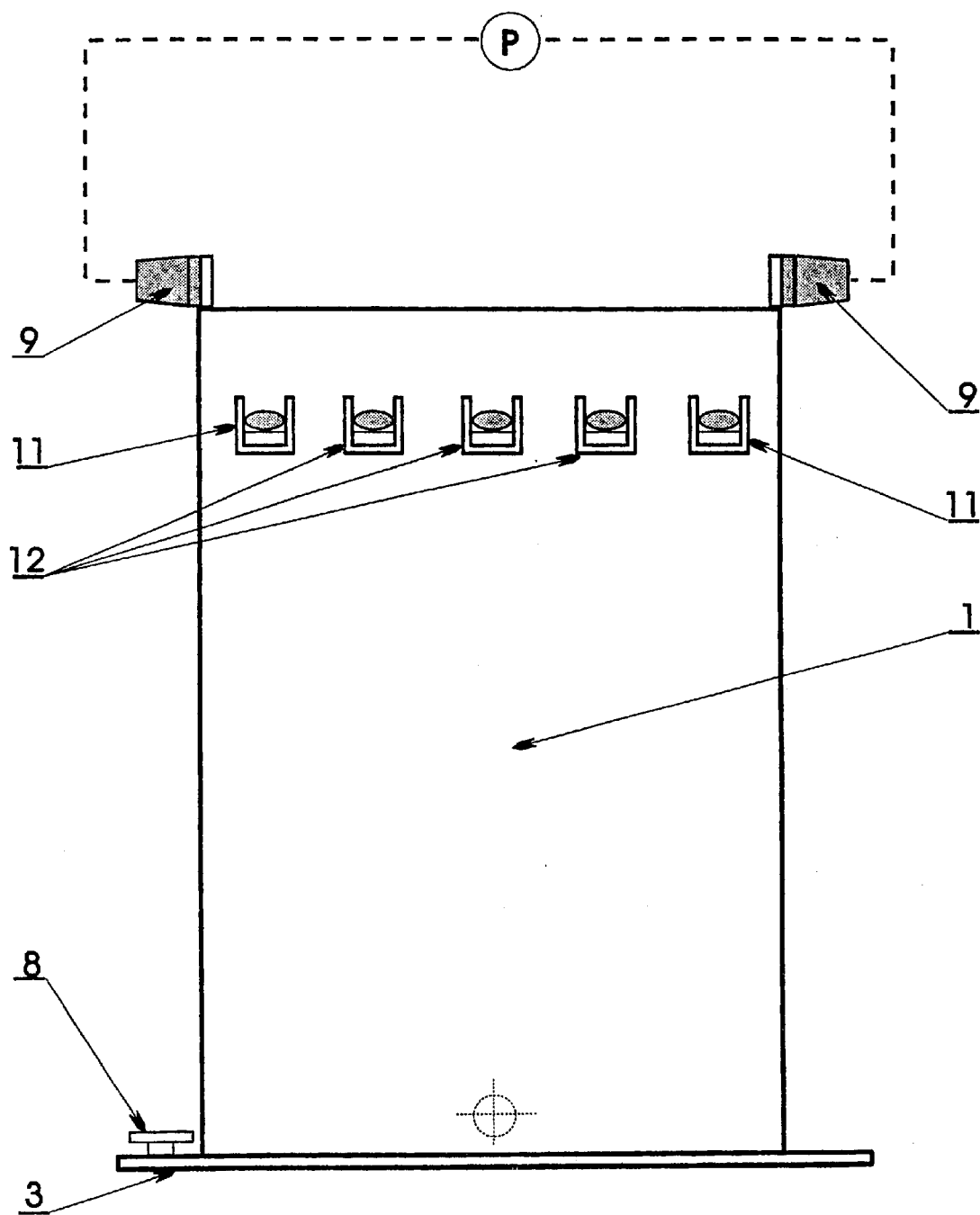
FIG. 2 is a vertical front view of the apparatus.
Figure 3:
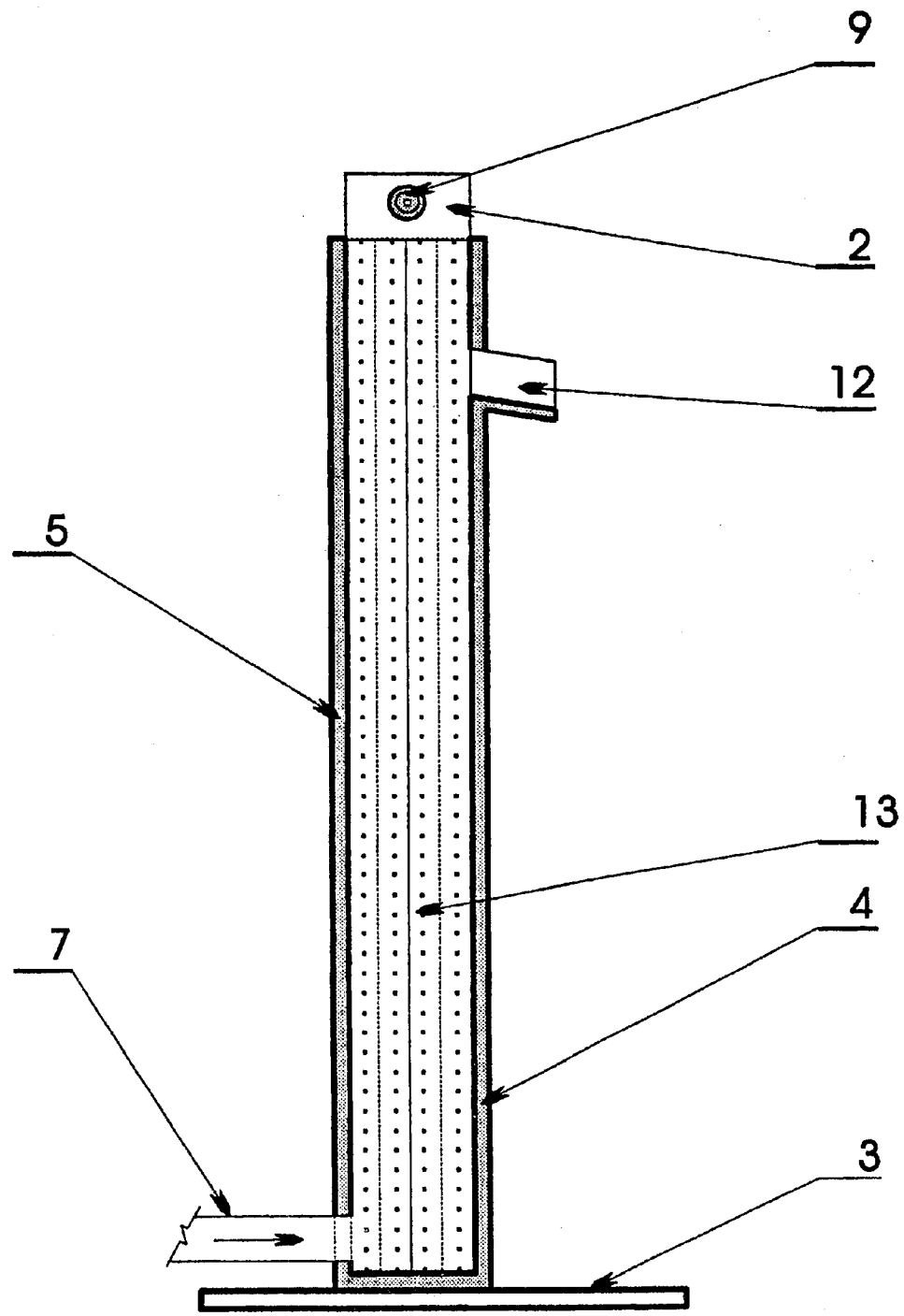
FIG. 3 is a vertical sectional side view of the apparatus taken along line 3—3/FIG. 2.
Figure 4:
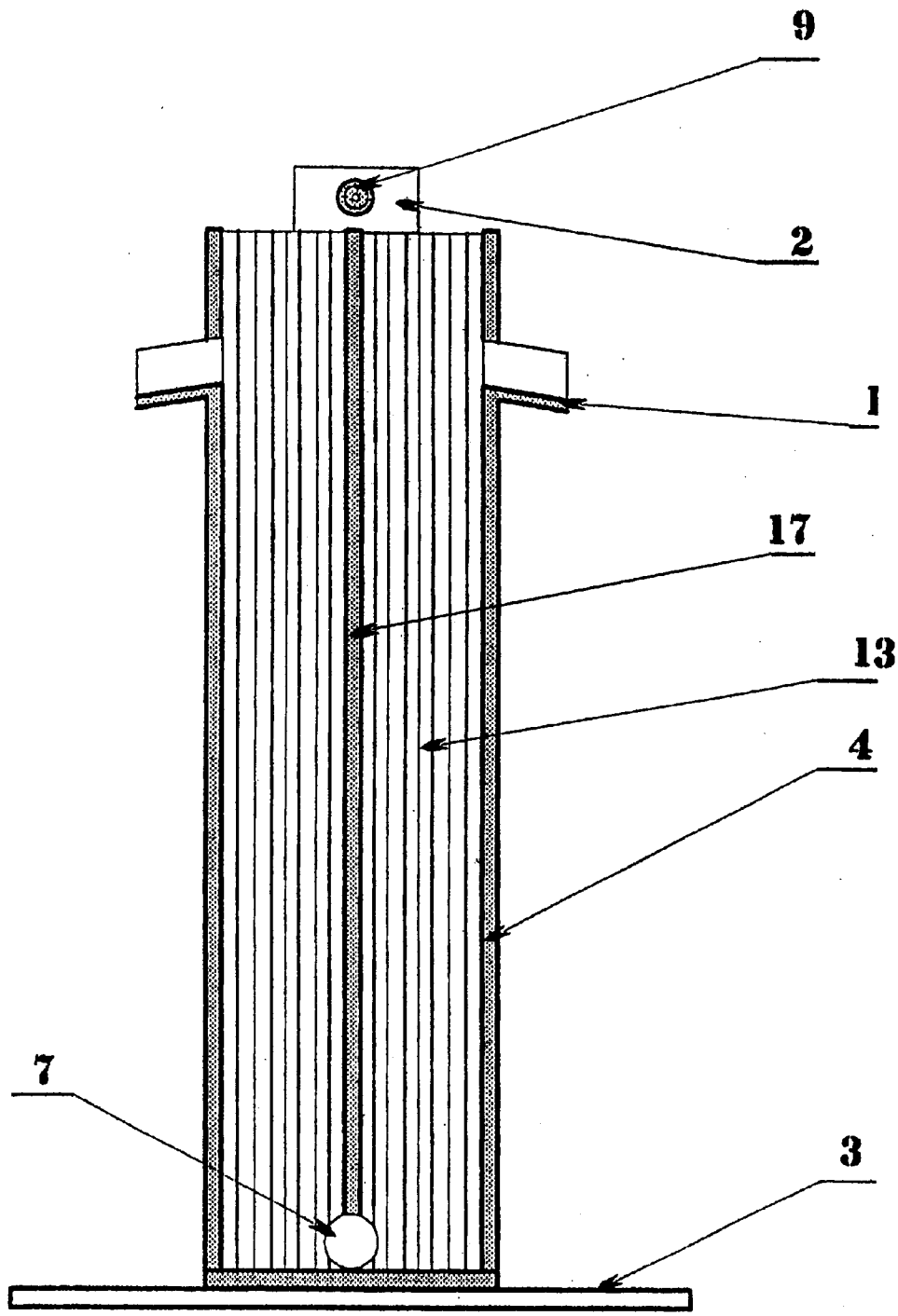
FIG. 4 is a vertical sectional side view of the apparatus in twin-configuration.
Figure 5:
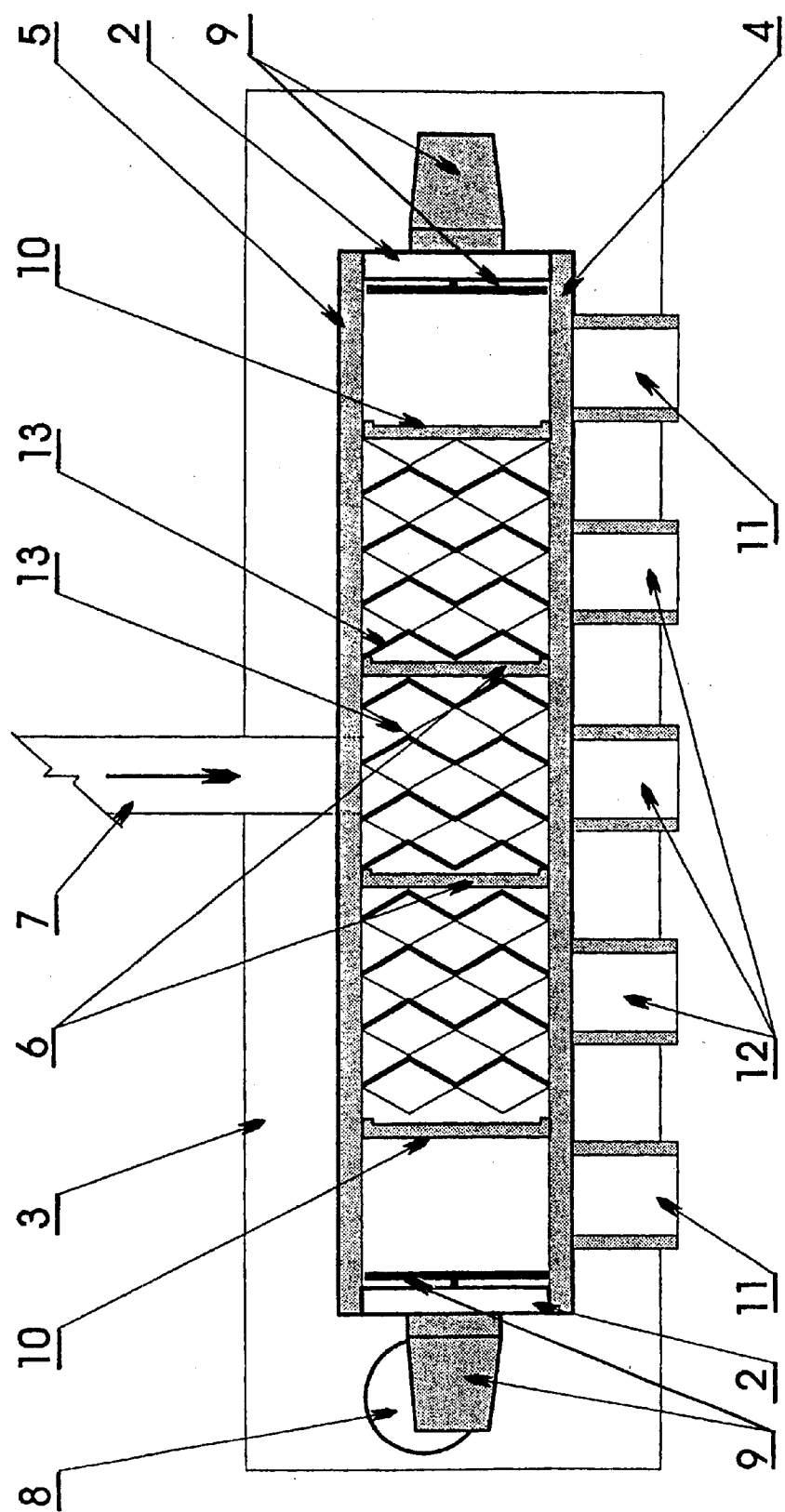
FIG. 5 is an overhead view of the apparatus with zig-zag partitions.
Figure 6A:
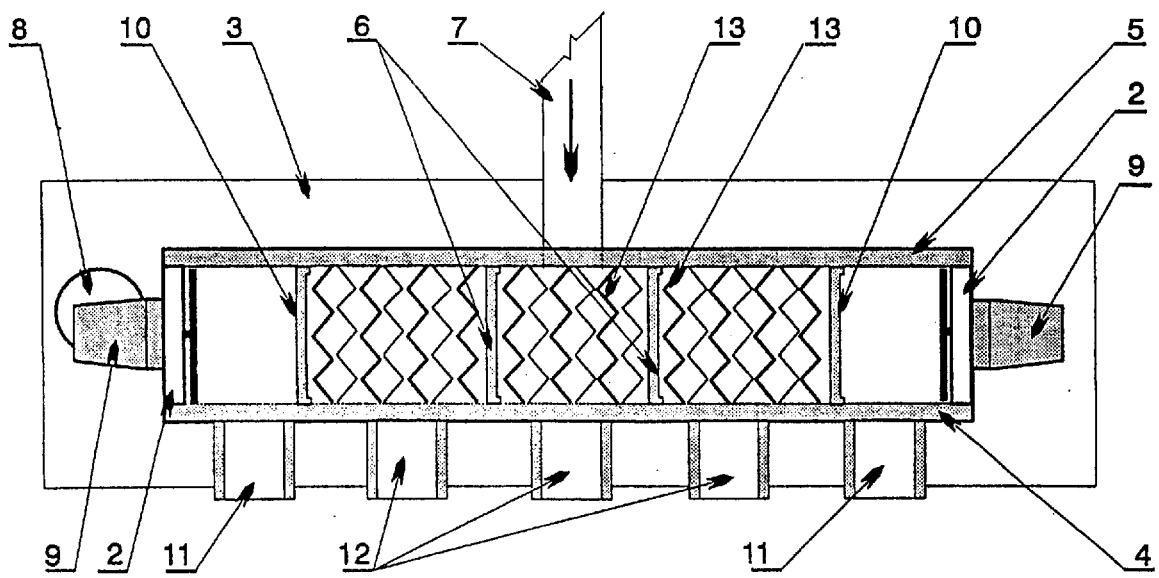
FIG. 6A is an overhead view of the apparatus with zig-zag partitions and FIG. 6B is a perspective view of a zig-zag partition.
Figure 6B:
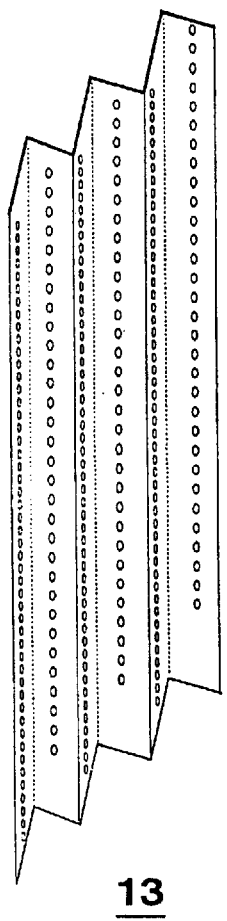
Figure 7A:
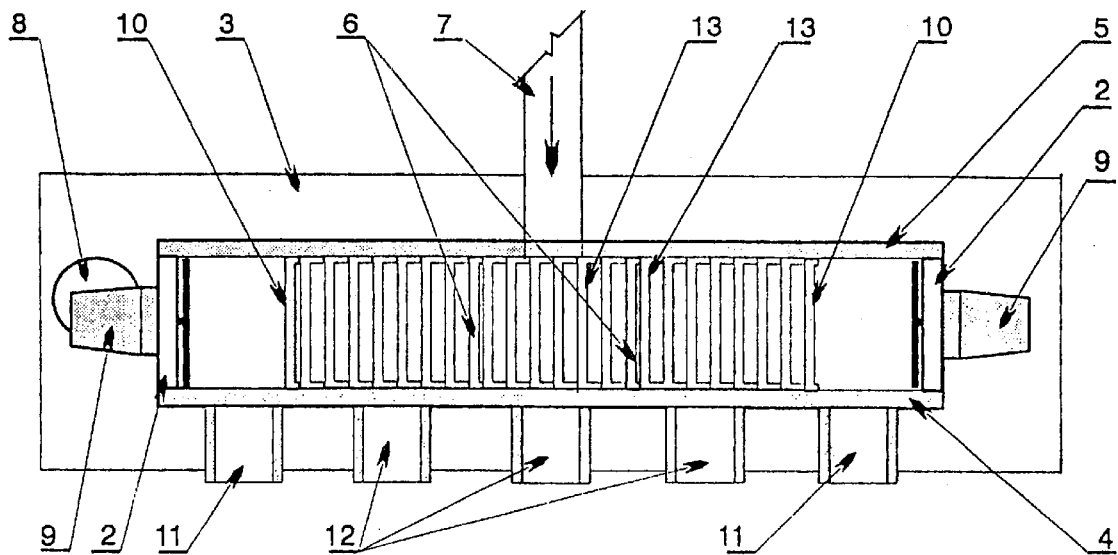
FIG. 7A is an overhead view of the apparatus with U-shaped partitions and FIG. 7B is a perspective view of a U-shaped partition.
Figure 7B:
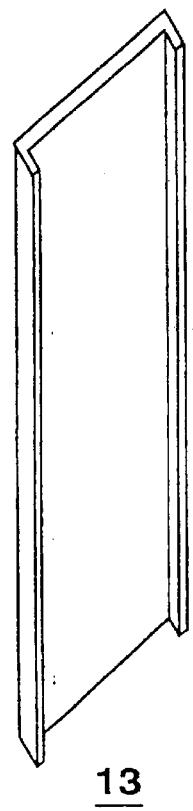

Apparatus for Continuous Flow Isoelectric Focusing, the Contifocuser

Reference will now be made to the drawings wherein like parts are designated with like numerals. Referring first to FIGS. 1–11, an apparatus 1 comprises a general rectangular electrochemically inert container having end walls 2, a bottom panel 3, a front wall 4 and a back wall 5. Apparatus 1 is provided with a partition 6 vertically attached to the back wall 5 and front wall 4 between every outflow port except for the electrode spaces outflows. These vertical partitions are holed or made of porous material in one third of their height from the bottom. The back panel 5 has one inflow port 7 at its bottom. The width of panel 3 W2 is greater than the width of apparatus 1 W1 (see FIG. 2). Both electrodes 9 are separated from other parts of apparatus by vertical ion-selective membranes 10, i.e., an anion-selective membrane near the anode and a cation-selective membrane near the cathode. The electrode spaces at the top of the apparatus have at one level with other working outflows 12 electrode outflows. The space between vertical partitions 6 in apparatus 1 is divided by a number of less preferred C-shaped, zigzag-shaped perforated, or by multiple U-shaped partition members (13) made of porous material which are placed apart at a distance of 1 cm, 0.5 mm, and 0.3 mm, respectively. The invention employs a source of liquid solution containing organic or biological substances to be separated, preferably with a conductivity between 50 and 5,000 $\mu$S/cm. Carrier ampholytes to establish a suitable pH gradient are not used. The flow from source 14 can be regulated by a suitable valve 15, made of non-conductive material. The number of working outflow ports 12 will depend on the nature of the separation process applied. The separated solutions are collected from each of the ports 11 into a suitable container 16 as shown in FIG. 11. Apparatus 1 includes one levelling screw 8 located on one outer end of bottom panel 3, wherein screw 8 is for adjusting the horizontal level of outflow ports 12 on front wall 4. Apparatus 1 is provided with a pair of spaced electrodes 9 located adjacent to the end walls 2. Electrodes 9 extend from substantially the bottom of apparatus 1 to the top rim and are mounted in such a way as to be easily inserted and removed such as by a plurality of retaining brackets. Electrodes 9, which are an anode or a cathode, terminate in electrical connectors or plugs situated at the tops of end walls 2 in order to facilitate coupling electrodes 9 to an external power supply, shown as "P" in FIG. 2. Electrodes 9 are preferably chemically inert as well as being stable against cathodic and anodic dissolution in the same solution under applied bias conditions. Platinum and carbon have been used satisfactorily. Additionally, the apparatus walls are preferably formed from or coated with a chemically and electrically inert material such as teflon, acrylate, ceramic material or glass.

Referring to FIGS. 5, 6, 7 and 8, apparatus 1 is provided with a plurality of liquid permeable, vertical C-shaped, zig-zag or U-shaped partition members 13 which extend vertically between the bottom of apparatus 1 and a point just below the level of outflow ports 11 and 12 and extend horizontally among waterproof-mounted partitions 6 and 10, except in the electrode spaces. C-shaped or zig-zag partition members 13 include a plurality of openings or holes with a diameter 0.5 to 1 mm, which are equally spaced along the vertical dimension thereof. The U-shaped partition members 13 are made of porous material at about 50 $\mu$m. The vertical partitions 6 are substantially the same height as the apparatus 1.

The electrode spaces dividing partitions (vertical ion-selective membranes) 10 are mounted waterproof and their role is that the low molecular anions and cations will pass through ion-selective membranes from the working chambers to either the anodic space or the cathodic space. The small opening at the base of the partitions permits a limited flow of the solution through the electrode spaces for washing-out the concentrated ions. The vertical partitions 6 are waterproof-mounted in their upper third. Their function is important for apparatus construction an for good separation of liquid fractions separated during the flow through the apparatus in the last step—before leaving the apparatus through working outflows 12. The perforated vertical partition members 13 serve various purposes. Firstly, the holes or openings provide horizontal fluid flow across the apparatus 1. The second function of the holes is to provide pathways for the formation of a plurality of horizontal ionic current flow paths between electrodes 9 when a voltage is established there between. Moreover, the multiple U-shaped or zig-zag form of the vertical partition members 13 facilitates the formation of vertical flow channels in apparatus 1 (FIG. 3, 4 and 5) which allow for a continuous laminar flow upwards from the bottom to the upper part of apparatus 1. Finally, vertical partition members 13 suppress turbulence and convection horizontally across apparatus 1 between electrodes 9.

Figure 9:
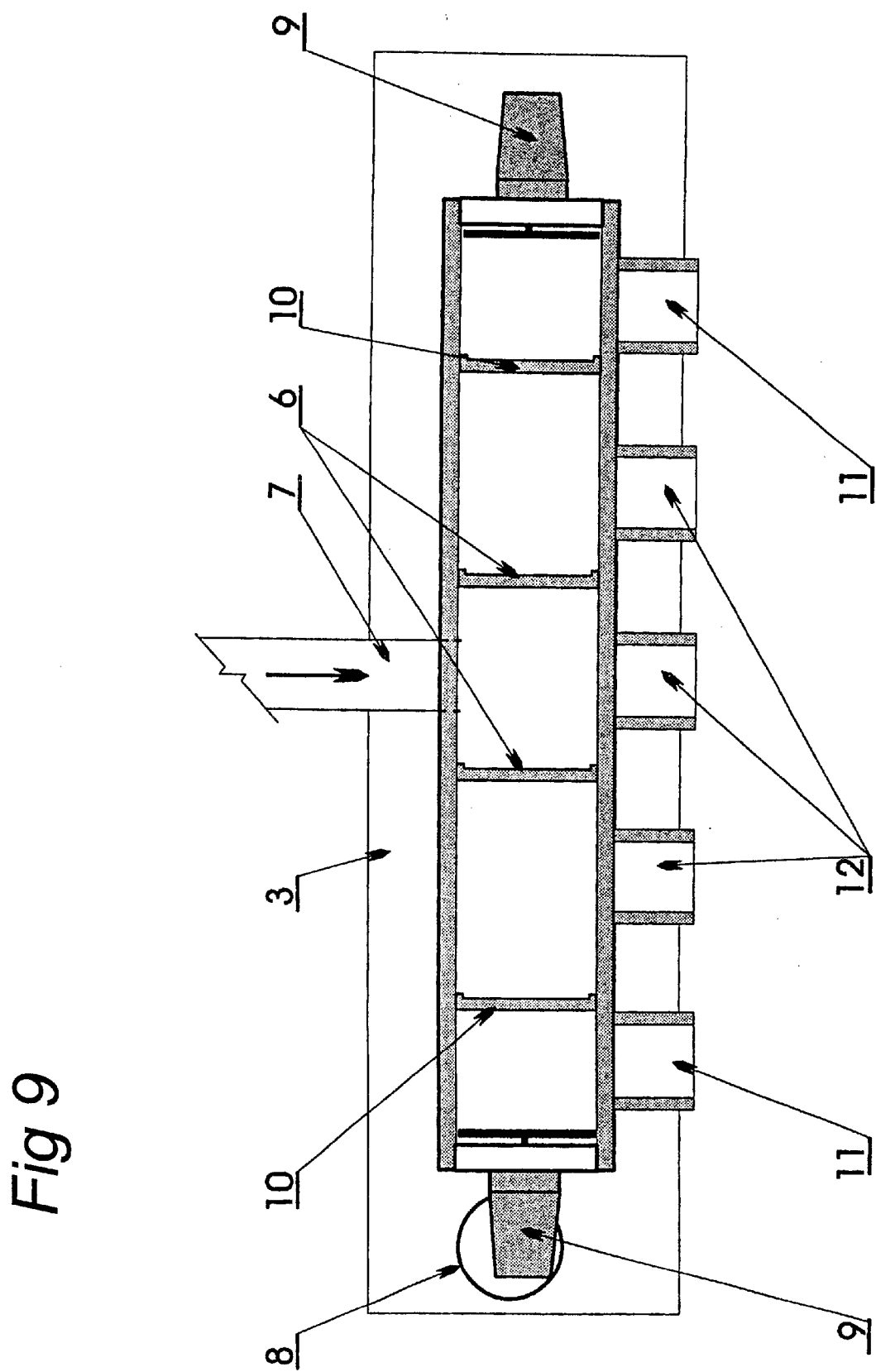
FIG. 9 is an overhead view of the apparatus showing four mounted partitions.

Referring to FIG. 9, apparatus 1 has the vertical partitions 6 sealed along their outer edges to front wall 4 and back wall 5 between two neighbouring working outflows 12 to form a liquid impermeable seal. The dimensions of each of the sub-chambers are provided with a plurality of vertical partition members 13, and are divided by vertical partitions 6, corresponding with the working outflows 12. In operation, a mixture containing the substances to be separated is suspended or dissolved in distilled water and the concentration of the starting substance shall have a conductivity in the range of 50–5,000 mS/cm. Apparatus 1 is then filled by a constant inflow of the solution or suspension into inflow 7. When the apparatus 1 is filled to a level just below ports 11–12, the inflow of solution is terminated and levelling screw 8 adjusted so that outflow ports 11–12 are horizontally aligned. Electrodes 9 are then connected to external power supply "P" and a direct current (DC) potential drop applied between electrodes 9 and the solution into the apparatus 1 is established. The horizontal flow of the compounds of the solution into apparatus 1 is established because of the electric low-current between electrodes 9.

During contifocusing, the components of the solution to be separated automatically form a pH gradient, horizontally across the apparatus, whilst the various zwitterionic components comprising the starting substance are driven or focused to a position in the apparatus having a pH corresponding to their own pI value or isoelectric point. The strongly polarised low-M.W. impurities are focused into the electrode spaces and are eliminated from the apparatus through the waste outflows of the electrode spaces. Once the components are separated and neutralised at their own pI, they become immobile in the electrical field in the horizontal direction, but are still flowing vertically upwards in flow channels between the vertical partition members 13 towards the upper part of apparatus 1. These exit via working outflow ports 12, and are collected or discarded. Alternatively, the solution can be recycled into the original solution, container 14, or into another contifocuser placed in series. The number of outflow ports 12 of apparatus 1 depend on the number of components to be separated. When various components with different isoelectric points have to be separated, a greater number of outflow ports can be used. In order to make the contifocuser versatile for different substances, apparatus 1 can be constructed with several outflow ports 12 with sliding members mounted on the interior of front wall 4 to open or close the outflow passageway through ports 12.

Normally, the flow rate per minute is maintained at 1/10th of the chamber volume of apparatus 1. The relation between the flow rate and the volume of apparatus 1 holds also for the apparatus 1 in which the volume is larger by increasing the height whilst maintaining the width of apparatus 1 constant. The time required for horizontal migration of charged components in the electric field remains the same. Therefore, increasing the vertical height of the apparatus permits higher flow rates. If the components have pI values which are close to each other it might be necessary to increase the resolution with respect to pH gradient to be formed. This is done by a greater horizontal length of the apparatus, requiring a longer horizontal migration time of the components and a lower-flow rate.

Another factor that determines the upper limit of the flow rate is the establishment and maintenance of a stable pH gradient across the working space of the apparatus. When the amphoteric impurities within the solution have a distinctly lower M.W. than the target substances, the pH gradient is established in a shorter time than the transit time of the components to be purified. The low M.W. components move faster. In addition, those with extreme pI values (<pH 2->pH 12) move into the electrodes spaces via the ion-selective membranes, and are discarded through the waste outflows. Therewith, the pH gradient in the apparatus, which was initially based on the low molecular impurities, is later maintained by the higher M.W. components.

Figure 10:
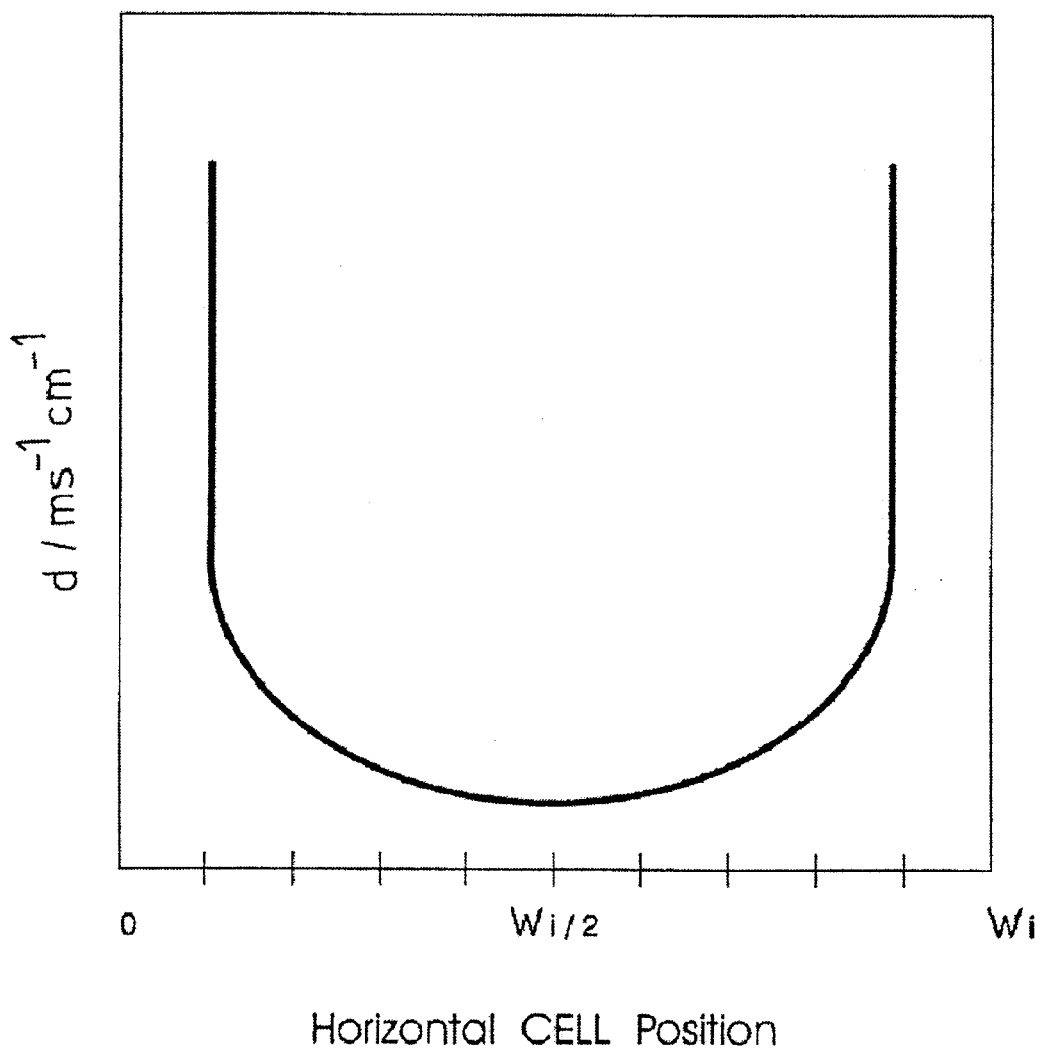
FIG. 10 is a plot of the conductivity across the width of the apparatus in operation.
Figure 11:
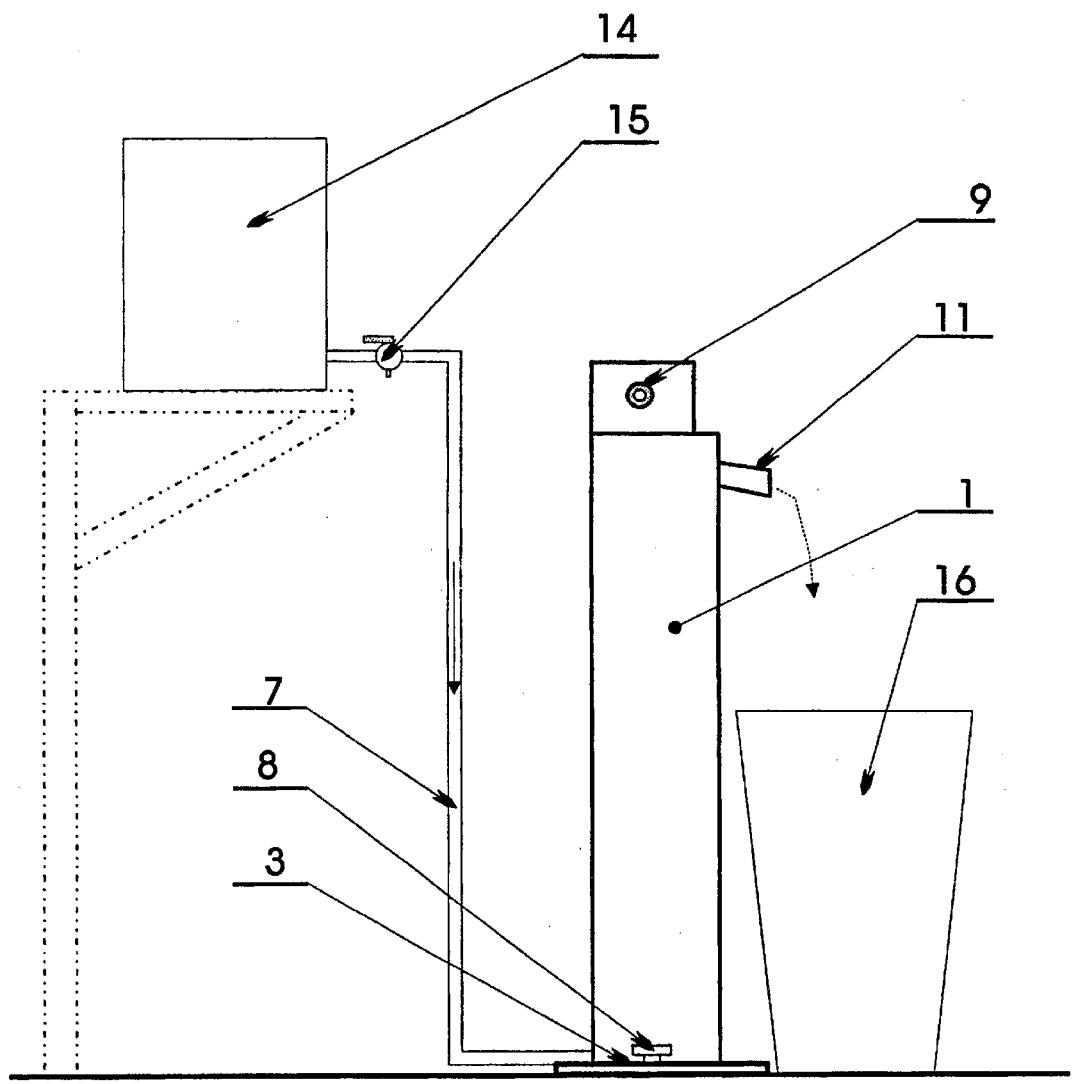
FIG. 11 is a schematic side view of the apparatus of the invention.

FIG. 10 illustrates the steady state conductivity profile across apparatus 1 in operation and shows that the conductivity is minimal in the working space and high in the electrode spaces in which the low M.W. and charged components are concentrated. This illustrates the usefulness of the contifocuser for elimination of impurities from neutral liquids such as water, beverages, and organic solvents.

The apparatus of the present invention uses simply a static electric field, and can operate for several days unattended since there are no electrochemical or other devices that require continuous attention of an operator. The power that results in optimum operating characteristics for most contifocusing applications, i.e. a fast separation time with minimum ohmic heating, lies in the range of 3–50 W.

Industrial Purification of Earthworm Enzymes

The present invention can be used for purification of enzymes from invertebrates such as the Californian earthworm *Eisenia foetida*, and a number of non-limiting examples for industrial application will be presented. The enzymes are produced as follows: earthworms are grown on agricultural offal, ingest and excrete the entire heap, and biohumus or vermi-compost is made. An attractant serves to separate the worms from biohumus, the worms are washed with tap water, are frozen at −20° C., and are homogenised in distilled water. The worm populations are selected by survival breeding for producing the desired enzymes at higher concentrations.

A contifocuser in twin-configuration (2×25 L volume) is used with a through flow capacity of 2.5 L/min (3,600 L/day). Daily a total of 2,000 L purified enzymes can be harvested from four working outflows (waste outflows are in between). A second contifocusing run is used for further purification. The protein concentration of both contifocusing runs yields a protein concentration of 1 g/L. The final yield of about 1,200 L/day has an average enzyme activity of 80 to 170 U/ml. This compares favourably with enzymatic activities of similar products based on bacterial fermentation. At the 25th Salon International des Inventions, Geneva, Switzerland, April 1997, a 10 L contifocuser was awarded with a golden medal for earthworm enzyme purification and for purification of vodka.

EXAMPLE 1

Isolation and Purification of Natural Enzymes From *E. Foetida*

Five novel types of purified non-bacterial enzymes are obtained from *E. foetida*. The enzymes for this Example were prepared as follows: Ten kg of a genetically selected strain of *E. foetida* were collected. The worms were frozen at −18° C. for 24 hrs and then thawed in cold water at 4° C., containing 0.1% glyoxal. This crude suspension was, portion after portion, mixed in a high capacity blender and homogenised in 100 L distilled water. The solution was centrifuged in a continuous flow centrifuge, and the supernatant introduced into a 2 L. apparatus according the present invention with ten outflow ports. A voltage of 250 V DC, a 80 mA electrical current, and an initial flow rate of 100 m/min was established. All manipulations were carried out at 4 to 10° C. The contifocusing run lasted 16 hrs. The solution from the working outflow ports were separately collected, corresponding to the isoelectric points of 8.3, 7.0, 6.5, 3.2 and 2.8. Each active enzyme fraction obtained by preparative SDS electrophoresis was hydrolysed by mineral and peptic hydrolysis, and the amino acid residues were measured by an automatic amino acid analyser. Three analyses were counted, and the average number and percentage of amino acids calculated. The five enzymes, in the order of decreasing pI values, are:

Eisenase—A basic enzyme mixture having proteolytic activity, a pI of 8.3, a pH optimum of 6.0, an M.W. of 17 kDa and an azocasein-splitting activity of 100–120 U/mg (one unit will hydrolyse sulphanilamide-azocasein (Merck Catalogue p.142, 1992) to-produce a colour equivalent by Folin-Ciocatteau reagent to 1.0 mM (=181 mg) of tyrosine per min at pH 7.5 and at 37° C. A unit (U) of azocasein-splitting activity as a measure of proteolytic activity is further defined as the amount of enzyme which can split 1 mM of azocasein per min as estimated by UV spectroscopy at 370 nm (Tomarelli et al., J. Lab. Clin. Medicine 34, 428, 1949). This enzyme is designated "eisenase", and has characteristics as mixed endo- and exopeptidase with serine and metalloproteolytic activity as described in the "International Enzyme Classification Catalogue", ECC sections 3.4.21.1, 3.4.21.4, 3.4.23.6, 3.4.21.14. It can be used as a natural preservative e.g. in meat packaging, and for topical skin treatment.

Fellulase—An enzyme having cellulolytic activity as well as proteolytic, and particularly slight fibrinolytic, activities, a pi of 7.0, a pH optimum of 5.9, and an M.W. of 67 kDa. This enzyme is designated "fellulase", and has characteristics of ECC section 3.2.1.4. The cellulolytic activity is about 10–20 U/mg (one unit liberates 1.0 mM of glucose from cellulose in one hr, at pH 5.0 at 37° C.). Fellulase exerts its cellulolytic activity in a low-acidic environment.

Purified samples of the five enzymes described in this example were analysed for their functional and physical protein characteristics. The data are summarised in Tables 1 and 2.

TABLE 1

Functional and physical protein characteristics of *E. foetida* enzymes

|  | Eisenase | fellulase | fetilase | Fetipase | wormase |
|---|---|---|---|---|---|
| pI[a] | 8.3 | 7.0 | 6.5 | 3.2 | 2.8 |
| pH Optimum | 6.0 | 5.9 | 7.2 | 4.6 | 3.6 |
| range ≥ 50%[b] | 4.2–8.1 | 4.4–7.1 | 5.8–8.6 | 3.6–5.9 | 2.7–5.3 |
| T optimum ° C. | 50 | 45 | 60 | 50 | 50 |
| Range ≥ 50%[b] | 25–60 | 10–55 | 30–65 | 25–60 | 5–70 |
| M.W. kDa (gel)[c] | 17 | 67 | 36 | 18 | 31 |
| M.W. kDa (calc.)[d] | 13.2 | ±54 | ±29 | ±14.5 | ±25 |
| Aminoacids[e] | 110 | 446 | 240 | 120 | 205 |
| % of basic a.a. | 23 | 4 | 6 | 25 | 15 |
| % of acidic a.a. | 0 | 7 | 5 | 7 | 22 |
| Proteolytic[f] | + | + | –[n] | +/– | + |
|  | Ser; Asn |  |  |  | Arg; Trp |
| α-amylolytic[g] | –[n] | – | + | – | – |
| β-amylolytic[h] | – | – | + | – | – |
| Cellulolytic[i] | – | + | – | – | – |
| Lipolytic[j] | – | – | – | + | – |
| Fibrinolytic[k] | – | ± | + | ± | + |
| Michaelis (mM)[m] | 1.76 | 0.85 | 1.60 | 0.88 | 0.35 |

[a]Isoelectric point determined by contifocusing.
[b]Range with ≥ 50% activity of the maximum activity.
[c]Determined from SDS-PAGE.
[d]Calculated from amino acid content (non-glycosylated).
[e]Total number determined by complete hydrolysis.
[f]Determined by activity on polyserine, polyarginine, polytryptophan and poly-Trp,Arg
[g]Determined by activity on starch at 37° C. and at pH 6.9
[h]Determined by activity on starch at 20° C. and at pH 4.8 (In this study by preparative SDS electrophoresis only β-amylase was obtained, in one enzymatic active line. The loss of β-amylase might be due to dissociation in SDS).
[i]Determined by activity on cellulose azure (Merck) Femley, N. H., Biochem. J., 87, 90 (1963)
[j]Determined by activity on Triglyceride No. 339 (Merck)
[k]Fibrine Plate Assay of Haverkate and Brakman (In: Progress in Fibrinolysis and Thrombolysis, Eds. Davidson, Samana, and Desnoyers, Raven Press, New York, Volume 1, pp. 151–159 (1995)
[m]Michaelis constant determined on the specific substrate for each individual enzyme.
[n]Indicating an enzyme activity in the order of 0.1 U.

TABLE 2

Amino acid composition of *E. foetida* enzymes (values ± 5%)

| amino acid | Eisenase | Fellulase | fetilase | fetipase | wormase |
|---|---|---|---|---|---|
| number of a.a. | 110 | 240 | 446 | 120 | 205 |
| Ala | 4.46 | 12.3 | 15.8 | 2.6 | 3.3 |
| β-Alanine | 0 | 3.7 | 0.7 | 4.1 | 4.8 |
| Arg | 10.30 | 2.0 | 1.0 | 6.8 | 3.2 |
| Asp + Asn | 17.24 | 4.0 | 0.9 | 5.8 | 12.3 |
| Cys | 6.89 | 4.0 | 1.2 | 0 | 1.7 |
| Glu + Gln | 6.89 | 5.5 | 7.6 | 8.3 | 12.9 |
| Gly | 13.79 | 14.5 | 12.1 | 7.5 | 6.5 |
| His | 3.45 | 4.0 | 2.9 | 8.5 | 8.1 |
| Ile | 2.50 | 2.0 | 0 | 0 | 1.6 |
| Leu | 3.45 | 10.2 | 9.9 | 6.8 | 3.2 |
| Lys | 10.34 | 0 | 0 | 8.5 | 3.2 |
| Met | 3.45 | 0 | 0 | 4.1 | 4.8 |
| Phe | 3.45 | 6.2 | 4.1 | 2.2 | 3.2 |
| Hydroxy-Pro | 0 | 0 | 0 | 8.5 | 8.1 |
| Pro | 0 | 0 | 15.2 | 10.2 | 9.7 |
| Ser | 3.45 | 12.0 | 10.7 | 5.1 | 3.2 |
| Thr | 0 | 3.6 | 2.4 | 0.7 | 1.6 |
| Trp | 0 | 2.0 | 2.0 | 1.7 | 1.6 |
| Tyr | 6.89 | 0 | 0 | 5.1 | 4.8 |
| Val | 3.45 | 14.0 | 13.6 | 3.4 | 1.6 |

Fetilase—An enzyme having α- and β-amylolytic, proteolytic and and particularly fibrinolytic activities, a pI of 6.5, a pH optimum of 7.2, an M.W. of 36 kDa, and an azocasein-splitting activity of 80–100 U/mg. This enzyme is designated "fetilase", and has characteristics of ECC sections 3.2.1.1, 3.2.1.2, 3.4.22.6. The amylolytic activity of fetilase is about 20–40 U/mg (one unit liberates 1.0 mg maltose from starch in 3 min, at pH 6.9 at 37° C. (P. Bemfeld: "Methods in Enzymology 1, 149, 1955). Fetilase can be used as a substitute for low barley amylase in the beer brewing process, and as a substitute for pancreatic enzyme in medicaments.

Fetipase—An enzyme having lipolytic and a slight proteolytic activity, a pI of 3.2, a pH optimum of pH 4.6, an M.W. of 18 kDa, and an azocasein-splitting activity of 80–100 U/mg. This enzyme is designated "fetipase", and has characteristics of ECC sections 3.1.1.1., 3.1.1.3, 3.4.22.6. The lipolytic activity of fetipase is 20 U/mg (one unit hydrolyses 1.0 meq. of fatty acid from a triglyceride per hr, at pH 7.7 and at 37° C. Fetipase can be used as an active substance in washing compositions.

Wormase—An acidic enzyme mixture having proteolytic and particularly fibrinolytic activities, a pI of about 2.8, a pH optimum of 3.6, an M.W. of 31 kDa and an azocasein-splitting activity of 80–100 U/mg (one unit will hydrolyse casein to produce a colour equivalent to 1.0 mM (181 mg) of tyrosine per min at pH 7.5 and at 37° C. This enzyme is designated "wormase", and has characteristics according EEC sections 3.4.23.1, 3.4.23.6, and 3.4.22.3. Wormase can be used in washing powders, in the food and beverage industry, in particular for splitting undesired proteins at a relatively low pH; in fruit juices, beer and wine a pH in the range of 3.9–6.0 is common. It reduces the protein content by about 70% and allows a reduction, or may eliminate, filtration steps in the production process of beverages.

Mixtures—The above-mentioned fibrinolytic activities were obtained with enzyme preparations that were purified with the apparatus according to the invention, and followed by a preparative SDS-PAGE. Fibrinolysis was observed in decreasing order for fetilase, wormase, fetipase and fellulase (see Table 1). The fibrin plate assay of Haverkate & Brakman was used (In: Progress in 5 Fibrinolysis and Thrombolysis. Eds. Davidson, Samana, and Desnoyers, Raven Press, New York, Vol. 1, 151–159, 1995). The slices of the SDS gel yielded only fibrinolysis in plasminogen-free fibrin plates and not in plasminogen-enriched fibrin plates. However, in the same fibrin plate assays performed with all five enzymes that were purified once or twice with the apparatus according to this invention, the fibrinolytic activity was observed both in the plasminogen-free fibrin plates as well as in the plasminogen-enriched fibrin plates. Moreover, the fibrinolysis in the plasminogen-enriched fibrin plates was even greater than in the plasminogen-free, fibrin plates. All fibrinolytic activities were higher than those of 0.75 CU/ml plasmid or of 50 ng/ml of a tissue-type plasminogen activator (t-PA, actilyse). These results indicate that, semi-purifide or mixture of the enzymes isolated in the apparatus according to the invention are able to degrade fibrin directly as well as to act as tissue-type plasminogen activator.(t-PA). The results suggest a synergistic effect between the five *Eisenia foetida* enzymes.

EXAMPLE 2

*E. Foetida* enzyme Mixtures for Industrial Purposes

Enzymmix—A multi-enzyme composition consisting of a mixture of wormase, eisenase, fetipase, and fetilase in a ratio of 30:40:15:15, and composed after one purification run using an apparatus according the present invention. The respective activities are as follows: wormase=65–90 U/ml; eisenase=80–100 U/ml; fetilase=60–90 U/ml; fetipase=60–90 U/ml. Enzy splits and degrades by hydrolysis mainly proteins, starch and lipids. Protein residues (from beer and wine), starch, muscle proteins (in meat and bacon) are partially split or degraded. An improvement of taste is obtained. Enzymmix can replace bacterial purification of wastewater, and without aeration. Enzymmix can be used in biological washing powders, washing powders, cleaning products, soaps, tooth pastes, shampoos etc. Enzymmix can be used in combination with a surfactant, see below. Enzymmix was able to reduce the concentration of polychlorobiphenyls (PCBs) in contaminated water from 40 to 5 mg/L. Enzymmix does not cause allergies, eczema or toxic effect for the human skin or body. It contains 30×less total protein than similar products produced by bacterial fermentation.

Enzymmix plus one-half volume of a long-chain ($C_{23}$) dicarboxylic acid surfactant, called "laurylan", with the mixture being referred to as "Recultol", is used for remediation of soil which is polluted by mineral oil contaminants in particular. This mixture can be applied directly on the soil, by spraying the afflicted areas twice, or can be added to water-enforced circulating in the sub-soil area. One ml of Recultol is able to split about 50 mg of contaminant. The average dose for soil to be remediated is 300–700 L/HA plus 150–300 L of laurylan. The mixture can also be used for cleaning of oil tankers since its enzymatic activity is not disturbed by higher salt concentrations. Remediation of oil spills on sea can be done with enzymmix bound to a carrier, preferably a degradable product, with a density that floats on top of oil phase and another with a phobicity for the water-oil phase. Both preparations may include a degradable colour, red or white, obtained from plants. The colour of the upper surface will alter from white to pink. In the case of solid surfaces, cement, concrete, railways etc., remediation by Recultol is done under high pressure with a mixture of 1 L of enzymmix and 1 L of laurylan in 1,000 L warm water (up to 50° C.). Preferably, Enzymmix is used in a composition that is applied in a method for remediation of soil and subsoil water, oil spills in seawater, for wastewater treatment, and for cleaning sea ships and tankers. However, a mixture of the enzymes wormase, eisenase, fetipase and fetilase where each enzyme is in a range of 15–40 parts, with the mixture being 100 parts total, is also suitable in a composition to be applied to a substance to be remediated.

Sanamor—A liquid washing composition which contains an enzyme mixture (wormase, eisenase, fetipase and fetilase), a surfactant, a disinfectant, and 0.1% glyoxal. Sanamor can be used for washing of pipes and equipment of the meat, milk and food industry. Sanamor is an alternative for acids and hydroxides which require high temperatures and have to be washed-out by large amounts of water. Sanamor has a dilution factor of 1:100 to 1:200, works at a temperature of 40° C. Only one wash with a standing time of 20 min is required. Sanamor has the additional benefit of eliminating deposits and tartar in the hidden corners of the pipes. It cleaves the organic stroma. Thereafter, the enzymes plus hydrolysed products are washed out by one rinse of the total pipe system. In this application of Sanamor for cleaning surfaces in slaghterhouses, milking machines, car washes, washing machines, bathrooms, floors, pipes, equipment and the like, the enzyme mixture present in Sanamor is preferably wormase, eisenase, fetipase and fetilase in a ratio of 25:30:25:20. However, ratios of the enzymes, where each enzyme is in a range of 20–30 parts with the enzyme mixture being 100 parts total, can also be used in Sanamor for cleaning surfaces.

Sanamor can also be used in a method for odor treatment and reducing ammonia emission, such as for reducing $NH_4$ emission in chicken houses by regularly spraying the chickens and their litter. Since about two-third of the $NH_4$ emission in the chicken house is generated by bacterial processing in litter, treatment of the litter is essential. Preferably, an enzyme mixture of wormase, eisenase, fetipase and fetilase in a ratio of 10:55:10:25 is used in Sanamor, although an enzyme mixture where each of wormase, eisenase, fetipase and fetilase is in a range of 10–55 parts, with the enzyme mixture being 100 parts total, can also be suitably used.

Enzymmix-F—A multi-enzyme composition consisting of a mixture of wormase, eisenase, fetipase, and fetilase in a ratio of 40:10:25:25, and composed after one purification run using an apparatus according the present invention. The respective activities are as follows: wormase=65–90 U/ml; eisenase=80–100 U/ml; fetilase=60–90 U/ml; fetipase=60–90 U/ml. Enzympremix is the same mixture, but the enzymes are now absorbed in a suitable carrier such as zeolite or bentonite. The feedmix can be administered to feed of broiler chickens and of pigs as growth promoter and to enhance feed conversion. It decreases amongst other things the energy required for the synthesis of the animal's own enzymes. During trials with Enzympremix, no side effects or toxicity were observed in the treated animals or in the animal caretakers. It was not possible to determine the lethal dose in mice because this material was apparently consumed as normal food.

For this Example, Enzymmix was prepared for a comparative trial in two groups of 20,000 broiler chickens of Omega BT Kft., 1078 Budapest, Hungary. Both groups were fed with baby starter feed during the first week of life, both groups received high energy feed with antibiotics from the second week onwards, and a final mixture without antibiotics during the last (7th) week. Water was supplied ad libitum. The only difference between the groups was the addition, during mixing of the feed mixture, of one L of Enzymmix-F to each ton feed supplied from the second day of life onwards. Significant differences were observed between the two groups after the desired bodyweight was achieved, all in favour of the group which received Enzymmix-F. The differences were: (1) Faster growth performance in shorter time, resulting in 200 g higher final bodyweight per bird (an average of 2,000 g obtained in 36 days vs. 1,800 g in 42 days), (2) 9.5% better feed conversion in the enzyme group, and (3) Reduction of total losses by 52% (total mortality of 5.5% vs. 11.5%). The combination of adding Enzymmix F to the feedmix and spraying of flocks and litter with Sanamor, with intervals of 4 days, resulted in a pleasant odour of the chicken house of the Enzymmix-F group. Herewith a significant lower degree of $NH_4$ emission was obtained but not precisely measured.

While Enzymmix-F and Enzympremix can be preferably used as a prebiotic, growth promoter or supplement to animal feed, suitable mixtures of the enzymes wormase, eisenase, fetipase and fetilase, where each enzyme is in a range of 10–140 parts with the enzyme mixture being 100 parts total, can also be used in a method for preparing a prebiotic or supplement to animal feed.

Dentamor—A multi-enzyme preparation for preparing a special enzymatic toothpaste containing proteolytic, amylolytic and lipolytic enzymes, e.g. equal parts of wormase, eisenase, fetipase and fetilase as well as Golden Yacca saponines (mercogenin, smilogenin, sarsagenin, gitogenin, neogitogenin and spirostan, ana partes 10 mg), all are saponines from the Mohave Yucca plant *Yucca Schidigera*, instead of only amylolytic enzyme and normally used synthetic surfactants. The spittle contains amylolytic enzyme only. But the food residues are better eliminated from and among the teeth when they are partially degraded by proteolytic and lipolytic enzymes as well. The enzymes have also a healing effect on paradentosis and gingivitis. In addition, it was shown that the Golden Yacca saponines are very powerful in elimination of toothstone.

Amor shampoos—Enzymatic shampoos of "Amor" are body and hair shampoos containing enzymes which are very smooth and careful against the skin and hair. Although the content of surfactants is lower than usual, these shampoos have a very high efficiency. During the development of a hair treating product, it was found that when the enzyme wormase was added to a commercial shampoo, less dandruff was observed after shampooing. Following this observation, various types of hair and body shampoos were developed:

AMOR—body shampoo containing proteolytic, amylolytic and lipolytic enzymes with a minimal content of self degradable surfactants, color and perfume.

AMOR H—enzymatic hair shampoo containing an enzyme mixture, anionic surfactant, color, perfume and saponines of Golden Yacca.

AMORLET—baby enzymatic shampoo where as a surfactant saponines of Golden yacca were used. A neutral pH and the exclusion of synthetic surfactants make that shampoo is gentle for the eyes of babies.

The formulations for the AMOR, AMOR H and AMORLET shampoos are as follows:

AMOR (body shampoo): Ethoxylated laurylalcohol, Altaran PT, Sodium alkyl.polyglycolether of sulphojantar acid (trietanol salt), Alvol OMK, Coco-dimethylaminoxid, Alvol AKD, Coco dieathanolamide, Sodium chloride, Glycerol, Enzymmix, Natural colour, Perfume, Lemon acid, Sorbic acid, Water (up to 100%).

AMOR H (enzymatic hair shampoo): Ethoxylated laurylalcohol, Altaran PT, Sodium alkyl.polyglycolether of sulphojantar acid (trietanol salt), Alvol OMK, Coco-dimethylaminoxid, Alvol AKD, Coco dieathnolamide, Sodium chloride, Glycerol, Lemon acid, Sorbic acid, Wormase, Natural colour, Perfume, Water (up to 100%).

AMORLET (baby enzymatic shampoo): Ethoxylated laurylalcohol, Altaran POA, Bisodium alkylpolyglycolether of sulphojantar acid, Altaran PT, Sodium alkylpolyglykoleter of sulphojantar acid (trietanol salt), Alvol OMK, Alvol AKD, Coco dieathanolamide, Coco-dimethylaminoxid, Sodium chloride, Enzymmix, Glycerol, Lemon acid, Natural colour, Perfume, Sorbic acid, Water (up to 100%), pH 7.00,

| where: | |
|---|---|
| Altaran PT | Sodium alky-polyglycolether of sulphojantar acid (triethanol salt) |
| Altaran POA | Bisodium alkyl-polyglycolether of sulphojantar acid |
| Alvol OMK | Coco-dimethylaminoxid |
| Alvol AKD | Coco diethanolamide |
| Alvol BLA | Lauryl amidopropylbetain |
| Alvol L | Lauryl alkanolamid |

| -continued | |
|---|---|
| Natural colour | Green = (from spinach), |
| Blue | from fruits of blueberry or bluish-black bilberries (*Vaccinium myrtillis* L.) Family: Ericaceae. |
| Perfume | Various fatty acids esters according to the wishes of the customer (citrus, green apple, forest mixture etc.). |

EXAMPLE 3

Isolation of Lysozyme

Lysozyme is an enzyme that is present in tears and egg white. For this Exarnple, egg white was collected from 2,000 eggs (about 50 L) and diluted in ice-cold distilled water, up to 150 L. All manipulations were done at 4° C. The solution was filtered and introduced into a 4 L apparatus according to the present invention, and having three working outflow ports (plus two electrode outflows). The contifocuser was initially filled with distilled water. The flow rate was adjusted at 75 ml/min, a DC 1,000 Volts was established, and the initial power of the system was 1.5 W. After adding the crude egg white suspension, the power raised to 10.5 W. The contifocusing lasted 34 hrs. Forty L of this material was collected from the working outflow port nearest to the cathode, at pH 10.5, containing lysozyme at a concentration of 200 U/ml. This suspension was gradually introduced into a 1 L contifocuser with three working and two electrode outflow ports. The flow rate with distilled water was adjusted at 10 ml/min, 1,000 V/DC. The initial output was 1.6 W but raised to 5 W after adding the lysozyme suspension. The contifocusing lasted 3 days. The outflow nearest to the cathode, at pH 10.5, was collected. The analysis yielded now a lysozyme activity of 1,500 U/ml. This fraction of 12 L was thereafter introduced in four fractions onto 200×1500 mm chromatographic columns packed by a molecular sieving gel, Spheron P-200, and 25 ml fractions were collected. In each, the protein content and the lysozyme activity were determined. Five protein peaks were observed. The first peak contained purified lysozyme at a protein-splitting activity of 20,000 U/g.

EXAMPLE 4

Isolation of α-amylase

*Bacillus subtilis* strains are of fundamental importance for basic science, medicine and industry. The entire genome has recently been sequenced (Nature, 390:237–1249, 1997) by joint efforts of several laboratories. The sequences of this sporeforming Gram-positive bacterium provides clues for antibiotic resistance of Gram-positive pathogens, and encode for several enzymes which have industrial application.

For this Example, *Bacillus subtilis* strain A-200 was cultivated in a 500 L fermenter vessel for 12 hrs at 37° C. The bacterial growth was arrested after a spectrophotometric measurement at 550 nm yielding a value >0.5. The bacterial mass was separated from the medium with a separator. The supernatant was introduced into a 10 L apparatus according to the present invention with three working outflow ports, including two outflows at both electrode sides. A flow rate of 250 m/min and 350 V of DC was applied. The electrode outflows were discarded, and the solution from the middle outflow was introduced into a second contifocuser of 5 L. Again an apparatus with three outflow ports was used, and the purified α-amylase collected from the middle. The flow rate was adjusted to 100 ml/min and 500 V of DC was applied The outflow port in the middle yielded relatively pure a-amylase with an amylolytic activity of 200 U/g.

EXAMPLE 5

Isolation of Insulin

For this Example, commercial insulin (NovoNordisk, DK) was suspended in distilled water, at 1 mg/ml. Three L of this suspension were introduced into a 1 L apparatus according to the present invention having five outflow ports (two electrode outflows and three ports for collecting a working solution). The conditions were: A 25 ml/min flow rate, 400 V DC, and an electrical current resulting in 8 W power. The contifocusing lasted two hrs. From the first working outflow port, near the anode, 800 ml of purified insulin was collected. A control PAGE analysis demonstrated in the original non-treated insulin preparation four lanes between 12–8 kB. After the contifocusing run only one lane at 10 kB was observed, corresponding to purified insulin. If the insulin needs to be further purified, an additional gel chromatography run can be arranged using a 100×500 mm chromatographic column packed with Spheron P-20. Purified insulin appears in the first protein peak.

EXAMPLE 6

Purification of Lysin

Technical grade lysin is available from different sources. It is used as a source of amino acids for upgrading feed for farm animals. If a higher purity of lysine is required, several complicated steps have to be made and the final product becomes more expensive. For this Example, five hundred L of technical grade lysin, diluted in distilled water to a concentration of 3was introduced into a 3 L apparatus according to the present invention with five outflows. The conductivity of this solution was 2,000 μS/cm. The purified lysin was collected from the first outflow port. This material had a conductivity of about 500 μS/cm, and the concentration of lysin was >15%. The loss of input protein material was about 5–10%, but this included the loss of impurities resulting from the original bacterial fermentation.

EXAMPLE 7

Isolation of Peroxidase

For this Example, a 1 L apparatus according to the present invention with two working outflow ports and two electrode outflow ports, was used for purification of horse radish peroxidase. Twenty kg of fresh roots were homogenised in 100 L of tap water. The unsoluble particles were removed by filtration. A 25 mM solution of gluthathion was added, and thereafter the homogenate was centrifugated to remove large particles. The conductivity of the solution was 1500 μS/cm. Ten L of this suspension was introduced into a 1 L contifocuser. The conditions were: A 50 ml/min flow rate, a DC power of 500 V, and an electrical current resulting in 15 W. The contifocusing lasted 3.5 hrs. The outflows from the electrode outflow ports were discarded. The outflows from the two working outflow ports were in the range between pH 5.5 and pH 6.6, and contained the peroxidase. This material was subjected to another 800 ml contifocuser run, now with only one working outflow port and two electrode outflow ports. The conditions were: a 50 ml/min flow rate, a DC power of 500 V, and an electrical current resulting in 10 W. The working outflow port in the middle yielded 25–30 U/ml of semi-purified peroxidase as demonstrated by spectrophotometric estimation. Further purification can be made by gel chromatography using a 100×500 mm column packed with Spheron P-20. Purified peroxidase appears in the second protein peak.

EXAMPLE 8

Purification of Whisky

For most alcoholic distillates, one or two distillation steps are required for elimination of various undesirable substances such as amyl acetates, ethyl hexanate, ethyl octanoate, ethyl decanoate, ethyl dodecanoate, that deteriorate the taste in particular. Elimination of these undesirable fractions can only be achieved by additional distillation procedures. The present invention provides a cost-effective purification. For this Example, whisky of a Canadian brand was introduced into a 10 L apparatus according to the present invention. The flow rate was 1 L/min, the DC power was adjusted at 1,000 V and 10 mA, resulting in 10 W. Three working outflows were used (two electrode outflows and one port in the middle). The whisky obtained from all outflow ports was subjected to a panel of specialists that judged differences in colour, smell and taste for the three outflows. Only the sample collected from the third outflow port required another distillation. The other two were mixed, and improved the quality and taste. Gas chromatography yielded a change of the single components as follows: amyl acetates, a decrease from 0.04 to 0.01 mg/100 ml, ethyl hexanoate from 0.05 to 0.02, ethyl octanoate—from 0.03 to 0.01, ethyl decanoate—from 0.025 to 0.001, ethyl dodecanoate—from 0.01 to 0.005 mg/100 ml.

EXAMPLE 9

Purification of Vodka

For this Example, vodka of local Slovakian and Dutch brands were purified. Twenty L was introduced into a 3 L apparatus according to the present invention. The flow rate was 3 L/hr, the initial DC power was set at 275 V and 80 mA, resulting in 22 W. Due to the elimination of electrolytes via the waste outflows, the conductivity decreased. The power was raised to 750 V as the current decreased, resulting in 12–18 W. Two working outflows were attached to 40% and 60% of the working chambers. An alcohol percentage of 41% was measured in the two working outflows as well as in the waste outflows. The vodka obtained from the first working outflow from the cathodic side had a "sharp" taste and may be used as "cleaning" alcohol. The second working outflow yielded vodka with a "soft" taste. The concentration of polyunsaturated fatty acids and of aldehydes decreased by 75% and 80%.

The contifocuser in twin-configuration for purification of vodka has a through flow capacity of 5 L/min and 7,200 L/day. A total of 6,800 L purified vodka is obtained per day. During this purification polyunsaturated fatty acids and aldehydes decrease by 68% to 88%.

EXAMPLE 10

Purification of Wine

Natural wines may contain high concentrations of acidic components. In addition, the quality becomes inferior by excessive fermentation or rotting caused by residual yeast products. The acid characteristics or artificial taste are difficult to eliminate employing the usual procedures. The present invention provides a technical solution for improving wine quality as demon-strated by this Example: 50 L of a Tocai wine, having an acid taste and a pH value of 3.8, was introduced into a 10 L apparatus according to the present invention. A 200 ml flow rate/min was adjusted and 250 V of DC was established between the electrodes. An apparatus with three working outflow ports, including two waste outflows, was used. The separation lasted 4 hrs. The outflows were subjected to a panel of professional wine tasters and judged for colour, smell and taste. The improved wine was collected from the working outflow port in the middle and from the cathode outflow port. The samples were mixed together and yielded an improved wine quality with a pH value of 5.2. Eighty percent of the input volume was recovered. The conductivity decreased from 1,670 $\mu$S/cm to 1,200 $\mu$S/cm, indicating that undesired charged low M.W. substances were eliminated.

EXAMPLE 11

Purification of Drinking Water

The last steps of purification are usually the most expensive or difficult. Bacterial contamination can be eliminated by absorption filters but chemical pollution are more difficult to handle, e.g. nitrites, nitrates, and various metals create greater problems.

For this Example, a 10 L apparatus according to the present invention with one working outflow port and two outflow ports near the electrodes was used. A through flow at 1 L/min was introduced. The DC power was adjusted at 100 V, and a current resulting in 25 W. As the analysis underneath indicates, the middle outflow port yielded purified drinking water, whilst the electrode outflows comprised the bulk of undesirable ions and elements. The loss of water volume was 15 to 20%. The results of the analysis of this experiment were as follows:

| Component | before | after |
|-----------|--------|-------|
| Copper    | 8.7    | 1.6   |
| Iron      | 12.3   | 1.2   |
| Nickel    | 0.05   | trace |
| Chromium  | 3.14   | 0.8   |
| Mercury   | 0.05   | trace |
| Zinc      | 71.0   | 12.4  |
| Arsenic   | 0.12   | 0.04  |
| Lead      | 0.71   | 0.05  |
| Cadmium   | trace  | none  |

The quality of drinking water obtained from the middle working outflow port can be regulated by adjusting the voltage, power and/or the flow rate. Purification and production of quality drinking water depend on the original water supply.

This invention provides a tool to achieve water purification on a relatively small scale, for example for households, caravans, farms and factories, at a minimal cost for energy and equipment. The maximum salt concentration that can be handled by an apparatus according this invention is about 900–1,200 mg/L. Therefore, desalination of seawater cannot be performed with this contifocuser. The maximum performance by one unit, with an internal volume of L, is about 150 L/day. If placed in parallel, e.g. five units can purify about 750 L/day. The chamber volume or the number of apparatus can be arranged for the conditions required, e.g. a calculation is made for a farm with 200 cattle that use deep-well drinking water. The cattle need about 40,000 L/day or 40,000:24:60=28 L flow rate/min.

EXAMPLE 12

Isolation of Immunoglobulins

12a. Mouse:

For this Example, we used 300 ml of a serum pool of mice that were immunised with rabbit IgG (Sevac, Prague). The serum was diluted 1:3 with ice-cold distilled water, and 1,200 ml of this solution was applied onto a 1 L apparatus according to the present invention with five pre-determined outflow ports. The contifocuser was initially filled with distilled water. The flow was adjusted at 8 ml/min, a DC power of 1,000 V was used and the initial output of the system was 1.6 W. After addition of serum, the power raised to 5 W as the result of increased conductivity. The contifocusing run lasted about 3 hrs. All five outflows were tested for immunoglobulins by immunoelectrophoresis. Immunoglobulins were detected at the second outflow port from the anodic side, between pH 4 and 6. The anti-IgG titre of this outflow was 1:128, as tested by a passive haemagglutination test using an antiserum against rabbit IgG. Of this material, 180 ml was introduced onto a chromatographic column, packed by Spheron P-200, and equilibrated by distilled water. Ten ml fractions were collected, and tested for the presence of immunoglobulins. Four protein peaks were demonstrated. Semi-purified immunoglobulins were present in a concentration of 0.5 mg/ml in the first peak. The passive haemagglutination test now yielded an anti-IgG titre of 1:1024. All samples from this peak were collected and concentrated for further use by freeze-drying.

12b. Human:

For this Example, a human serum pool with antibodies against hepatitis B virus antigens (HBsAg) was purified. Two L of serum were diluted by distilled water up to 8 L, i.e. dilution factor 1:4, and were saturated up to 8 M by urea; 0.1% of glyoxal was added. The final 10 L volume was introduced into a 1 L apparatus according to the present invention with four outflow ports. The flow rate was adjusted at 0.25 L/hr and the initial output of DC power was 10 W. After addition of serum, the power raised to 14 W. The contifocusing run lasted 5 hrs. The bulk of proteins, 8 mg/ml and including the specific antibodies, was collected from the second outflow port from the anodic side, at pH 5.6. A total of 2 L was collected. Immunoglobulins against HBsAg were present at a titre of 1:512 in the immunodiffusion test. The HBsAg antibodies were further purified by gel chromatography as follows: The semi-purified serum sample was divided into five parts of 400 ml, and each of them was introduced onto a separate chromatographic column, packed by Spheron P-200. Four protein peaks were obtained. The first peak contained specific antibodies. The total yield of specific antibodies from five gel o chromatography runs was collected and diluted in a total volume of 4,500 ml distilled water. Thereafter, the contifocusing run was repeated as above. Anti-HBsAg was now collected from two working outflow ports in the middle, at pH 5.1 and pH 5.4.

The present invention enables efficient preparation of an anti-antibody directed against the entire spectrum of immune responses induced by e.g. an enzyme, a protease, a toxin, or a viral or bacterial surface protein. In the network theory of immune regulation (Jerne: Ann. Immunol. 125: 373–389) the mimicry properties of anti-idiotype antibodies were described as the functional internal image of antigens.

12c. Swine:

For this Example, five pigs at a body weight of 100 kg were immunised with a commercial swine fever virus (SFV)

vaccine based on the Chinese C strain. The pigs were killed 5 weeks after immunisation and exsanguinated. A serum pool of 10 L was obtained by centrifugation at 800 rpm. The serum was 3×diluted in distilled water, and 30 L was saturated up to 8 M by urea; 0.1% glyoxal was added. This material was introduced into a 2 L apparatus according to the present invention with five outflow ports. The conditions were adjusted at a 100 ml/min flow rate and 250 V DC power at the beginning. The contifocusing run lasted 5 hrs. Specific antibodies against SFV were observed in the samples collected from two outflow ports, from the first working outflow port at pH 4.5 and from the second at pH 6.2. An SFV neutralisation (VNT) testkit (Sevac, Prague) was used (Since this was a totally unexpected observation, the original SFV vaccine was subjected to a contifocusing run as well in which was demonstrated that this SFV vaccine comprised two populations of SFV, probably comprising the SFV $E_2$ (gp55) and SFV $E^{RNS}$ epitopes which both induce neutralizing antibodies against SFV. The VNT showed that both virus peaks were SFV specific, and no contamination with BVD virus was detected). Thus, two anti-SFV serum fractions were obtained. Both fractions were freeze dried, then diluted in 0.9% NaCl in distilled water up to a protein concentration of 3 mg/ml, and were separately introduced onto chromatography columns packed with Spheron P-40, each in a single run. The pH 6.2 fraction yielded one protein fraction which had a VNT antibody titre of 1:512. The pH 4.5 fraction yielded four protein fractions after gel chromatography. Two peaks were SFV antibody-positive with VNT antibody titres of 1:64. The three single SFV antibody-positive fractions as well as all three SFV antibody-positive fractions combined will be used for immunisation of goats to investigate whether this invention can be used for preparing an anti-idiotype vaccine against swine fever.

EXAMPLE 13

Preparation of a Novel Sub-unit Vaccine Against *Escherichia Coli* Infections

According the prior art, a series of vaccines was developed directed against various adhesion factors of *E. coli*. For each adhesion factor a separate fermentation step was used. This Example describes a unique multifactorial recombinant sub-unit vaccine against *E. coli* infections of cattle, swine and sheep for which only one bacterial fermentation step is required. The second improvement is its manufacture according this invention using an apparatus according to the present invention with ten outflow ports: A genetically modified *E. coli* construct was made from a K 88 ab antigen-carrying *E. coli* strain G-7 (obtained from the Veterinary Faculty, University of Kosice, SK); a K 88 ac strain U-200 (State Veterinary University, Montevideo, Uruguay); a K-99 and an Lt enterotoxin antigen-holding strain S-IH (CZ Collection of Microorganisms, Bmo, SK), and from a 987-P strain (Dr. Salajka, Ivanovice na Hane, CZ). Plasmids encoding the antigens were cloned using the restriction enzymes BglI, BglII and Pst. Via analytical and preparative PAGE, DNA chains of 20–90 kDa were isolated and ligated by Lambda L4 ligase in various combinations. The constructs were transfected into a plasmid free *E. coli* strain H-110 by electroporation.

Two constructs were selected which encoded resistance against chloramphenicol and tetracyclines, and which contained all of the above-mentioned adhesion factors and enterotoxins. The integration and expression of K88 ab, ac, K99, 987/P and Lt enterotoxin genes was tested by haemagglutination tests. Fifty sequential bacterial cultivation steps were used to prove the stability of integration and expression for all foreign antigens. The modified *E. coli* strain H-110 was cultivated in a 300 L fermenter. After 8 hrs of cultivation, the bacterial culture was collected and subjected to centrifugation at 800 rpm. A total of 750 g of bacterial sediment was harvested and this material was subjected to shearing of the surface proteins (fimbriae) in 20 L ice-cold distilled water for 10 min. After the first shearing, the solution was centrifuged again at 3,000 rpm and the supernatant collected. The remaining sediment was diluted in 20 L ice-cold distilled water, 750 g of glass beads were added and mixed for 10 min. The surface proteins were further purified in a contifocuser with nine outflow ports, two near the electrodes, four working outflows, and three waste outflows in between. The conti-focusing run was performed at 75 ml/min flow rate, 500 V DC, 14 W, 4° C., and lasted 9 hrs. The solutions from the 2nd, 4th, 6th and 8th (working) outflow ports, corresponding to pH values ranging from pH 4.5–5.0, pH 6.0–7.0, pH 7.0–7.5, and pH 9.5–10.0, yielded respectively the purified fractions containing resp. K 88 ab, ac; 987-P; enterotoxin LT; and K 99 antigens. The titres are determined by a passive haemagglutination test, and the purified antigens can be diluted 5–10× to a titre of 1:512. Concentration steps are not required. A stable oil-emulsion was prepared including 0.5 mg/ml of K88 ab, ac, K99, 987/P, and Lt. enterotoxin antigens. An adjuvant (Specol®, 20% W/W, ID-DLO Institute, Lelystad, NL) and 0.1% glyoxal as further vaccine components were added. This novel recombinant sub-unit vaccine was used to vaccinate pregnant cows at 5 weeks before parturition in order to obtain passive immunity in offspring. The observed maternal antibody titres in calves were 2 to 3-fold higher than observed for prior art vaccines. A lower loss (1.5%) by *E. coli* diarrhoea and *E. coli* sepsis was observed. Challenge experiments with pathogenic *E. coli* strains (2 ml containing $10^9$ bacteria/ml) did not result in a higher mortality. This vaccine can particularly be used in husbandry operations where antibiotics are not available or not wanted for other reasons.

EXAMPLE 14

Purification of Polynucleotides

Prior art isoelectrofocusing procedures have been used for purification based on antibiotics resistance heterogeneity of DNA plasmids carrying adhesion factors of *E. coli*, a causative agent of *E. coli* diarrhoea and sepsis. For this Example, a small 0.5 L apparatus according to the present invention was used. DNA plasmids were isolated by standard procedures according to Maniatis et al., J. Bacteriology (1982), from *E. coli* strains F 027 (plasmid RMS 151), C 600 (RSF 1010) and J 53 (pSa). A 3% glycerol solution in distilled water was used for diluting the DNA plasmids. A volume of 1 L of each plasmid, containing about 7 μg of pure DNA/100 ml, was used for a contifocusing run with nine working outflows was used. The flow rate was 50 ml/hr. The separation lasted 10 hrs for each plasmid preparation. The following results were obtained: Plasmid RMS 151 was separated into two fractions, and these were demonstrated in the first and the third anodic outflow ports, at pH 2.7 and 4.1. On the basis of resistance against antibiotics was shown that isoelectric fractionation of plasmid DNA yielded fractions with different properties i.e. the original plasmid RMS 151 held a resistance against both tetracyclines and ampicillin, but now one fraction showed resistance against tetracyclin and the other against ampicillin only. Plasmid pSa was fractionated into three fractions, and which appeared in the first, second and third anodic outflow ports, at pH 2.1, 3.4 and 4.2 respectively. Plasmid RFS 1010, however, remained homogeneous after the contifocusing run, and only one fraction having resistance against both tetracyclin and ampicillin was collected from the second anodic outflow port, at pH 2.9. By UV spectrophotometric measurement was demonstrated that the plasmid concentration increased to 20–28 µg DNA/100 ml, indicating a 4-fold concentration of the original sample. A similar concentration was measured for each fraction of the RMS 151 and pSa plasmids.

The advantage of this invention for DNA purification is that purified plasmids are obtained on the basis of distinct pI values through different resistance against antibiotics, and at the same time a 4-fold concentration is achieved. Both are important for large-scale manufacturing.

EXAMPLE 15

Purification of Tetracyclin

Prior art isoelectrofocusing procedures according U.S. Pat. No. 5,256,269 were used to purify a commercial tetracyclin preparation obtained from Spofa CSFR (United Pharmaceutical Works, Roztoky, CZ). Tetracyclin was separated into four peaks with distinct colour and pH value. One fraction showed an increased bactericidal activity in the antibiotics resistance disk tests against *E. coli* and two Streptococcus Spp. In this test full bacterial growth around the disk is marked as "−", an empty area of the size of the disk as "+", absence of bacterial growth in an area of twice the disk size "++", and greater "+++". The semi-purified tetracyclin sample collected at pH 6.8 demonstrated 94% inhibition as compared with 85% for the original material. The fraction collected near the anode caused strong allergic reactions in mice after i.p. inoculation. By thin layer chromatography, and using probes against leukotrienes and arachidonic acid, was shown that the toxicity was due to leukotriens, polyunsaturated fatty acids, metabolites of arachidonic acid, that have three conjugated double bonds.

An apparatus according the present invention with eight working outflow ports was used for purification of the same brand of commercial tetracyclin. Two hundred grams (200 g) were dissolved in 2 L of 30% ethylalcohol and 70% distilled water, and introduced into a 800 ml. The flow rate was adjusted at 40 ml/min. The initial output of DC power was adjusted at 4 W. Four fractions collected from every odd outflow port were coloured, i.e. at pH 2.2 with a brown colour, at pH 6.8 with a bright yellow colour, at pH 7.9 with an orange-yellow colour, and at pH 9.2 with an orange colour. The outflows from the four outflow ports situated in between were not coloured. The bactericidal activities of the fractions were tested with the antibiotics resistance disk test against *E. coli* strain G-7 (see Example 12) and against *Streptococcus aureus*, CCM No. 644 527 (Czech Collection of Microorganisms). The fractions collected at pH 2.2, 6.8, 7.9, and 9.2 yielded bactericidal activity against both strains as follows: "−", "+++", "++", and "+". The outflows from the four ports in between had no bactericidal activity ("−"). These results indicate that a contifocuser in twin-configuration (2×25 L volume) can be used with a through flow capacity of 2.5 L/min (3,600 L/day). Daily a total of 360 L purified tetracyclin, and with increased bactericidal activity, can be harvested from the outflow port at pH 6.8.

EXAMPLE 16

Purification of Doxycyclin

An 1 L apparatus according the present invention with three working outflow ports and two electrode outflow ports was used for purification of doxycyclin, being a chemically modified tetracyclin. This antibiotic is used for broadspectrum oral treatment. Twenty-five gram (25 g) of doxycyclin, kindly provided by Amstelfarma BV, Lelystad, the Netherlands, was dissolved in 1 L of 90% ethylalcohol and 10% distilled water, yielding a 2.5% solution. The conductivity of the solution was 150 µS/cm. The DC power was at 1000 V and 5–8 mA, the flow rate was 5 ml/min and the contifocusing run lasted 120 min. Five fractions (Nrs. 1–5) were collected at pH 1.8, pH 4.0, pH 4.1, pH 4.4 and pH 5.6.

The anodic outflow at pH 1.8 had a slightly yellow colour, the outflows No. 2 and 3. a straw-yellow colour, and the two other outflows a more intense yellow colour. The bactericidal activities of the fractions were tested with the antibiotics resistance disk test against *E. coli* strain G-7, *Micrococcus luteus*, CCM No. 169, and against *Salmonella pullorum*. The bactericidal activities of the fractions Nrs. 1–5 were as follows:

| Fraction No. | 1. (anode) | 2. | 3. | 4. | 5. (cathode) |
|---|---|---|---|---|---|
| E. coli | "++" | "+++" | "+++" | "++", | and "−"; |
| M. luteus | "+" | "+++" | "+++" | "−", | and "−"; |
| S. pullorum | "−" | "++" | "+++" | "++", | and "+" |

The five fractions was tested for toxicity by intraperitoneal injection of ½ ml of each into ten mice (Wistar, female, of 20 g body weight). The reactions were recorded as follows: anaphylactic shock and death: "+++"; allergic attack but survival: "++"; slight allergic reaction: "+", no symptoms: "−".

Anaphylactic shock was observed in eight of ten mice inoculated with ½ ml of the anodic outflow, and died within 30 min (8/10: "+++"). Two of ten mice had an allergic attach but survived (2/10: "++"). No clinical symptoms, i.e. "−" scores, were observed in the four groups of ten mice that received ½ ml injections from the fractions No. 2., 3., 4., and 5 (cathodic outflow port). The fractions Nrs. 1–5 were tested by thinlayer chromatography for the presence of leukotriens. Standard precoated silicate plates, 15×15 cm (LKB, Sweden) were used in an ascendent arrangement. A 6.4 mM phosphate buffer was used. At the bottom of the plate, 50 µl of each fraction and the marker for leukotriens (SIGMA, cat. No. L-3526) were applied to the starting microholes. Then the applied samples were dried and the bottom of the plate immersed into the buffer solution. The ascendent chromatography lasted two hrs. The chromatography was interrupted, the plate was dried, and stained by spraying with a standard ninhydrine solution to detecting aminoacids and fatty acids. The anodic outflow at pH 1.8 yielded a spot with a RF corresponding with the RF of the leukotrien marker. In the other fractions these spots were not observed.

We conclude that the present invention enables the elimination of toxic substances such as leukotriens during the production process of doxycyclin. The outflow from the anodic outflow port has to be eliminated during the industrial production process due to the negative charge as well as the strong basic cathodic outflow (that contains minimal antibactarial activity). Further experiments will indicate the grade of concentration of bactericidal activity that can be achieved in fractions No.2 and No.3. Pilot studies can determine whether a similar enhancement of bactericidal activity and elimination of toxic products can be obtained other antibiotics. Prototypes can be developed for large-scale manufacturing.

EXAMPLE 17

Purification of Lactoglobulin From Milk

Five L of fresh cow milk was centrifuged at 3000 rpm for 15 min in a cooled centrifuge. The supernatant lipids were eliminated. Casein was removed after coagulation by adding 10 ml of chymotrypsine, and centrifugated as before. The whey (3.5L) was collected, and diluted with 6.5 L of distilled water. The conductivity of the solution was 900 $\mu$S/cm. This solution was introduced into a 1 L apparatus according the present invention with three working outflow ports and two electrode outflow ports. The conditions were as follows: a DC power of 500 V, 50 mA, and a flow rate of 10 ml/min. The contifocusing lasted 17 hours at 8° C. The outflow materials from all of outflow ports were collected with pH values, beginning at the anodic outflow port, as follows: pH 1.8, pH 3.9, pH 5.2, pH 7.6, and pH 12. According to the known isoelectric points of milk proteins (Righeti, P G and Caravaggio, T. J. Chromatogr. 1976, 127, 1–28) lactoglobulin was present in outflow at pH 5.2 in a concentration of 0.1–0.2 mg protein/ml.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A continuous flow apparatus for separating charged substances in liquid medium by isoelectric focusing, comprising a separating chamber (1), a pair of vertical electrodes (9) located in the separating chamber at the extremes of the cross-section thereof, an inflow port (7) at the bottom of said apparatus, two or more primary outflow ports (12) at the same height in the upper part of the chamber, a vertical partition (6) between each of said two or more outflow ports partitioning the chamber at least at the height of said outflow ports, characterised in that it further comprises a vertical cation-selective membrane (10) located near the cathode and a vertical anion-selective membrane (10) located near the anode for separating the electrode spaces from a central part of the separating chamber, said cation-selective and anion-selective membrane allowing the passage of low-molecular weight cations and anions respectively, from said central part to said electrode spaces, said ion-selective membranes (10) being essentially impermeable to high-molecular weight substances, a secondary outflow port (11) being provided in the upper part of the chamber in each of the electrode spaces, the apparatus further comprising vertical permeable partition members (13) disposed in the remaining spaces between one vertical partition (6) and another vertical partition (6) or between a vertical partition (6) and a vertical ion-selective membrane (10) that are structured so as to prevent horizontal turbulence.

2. The continuous flow isoelectrofocusing apparatus according to claim 1, wherein said vertical permeable partition members (13) are U-shaped.

3. The continuous flow isoelectrofocusing apparatus according to claim 1, wherein said vertical permeable partition members (13) are zigzag shaped.

4. The continuous flow isoelectrofocusing apparatus according to claim 1, comprising at least three of said primary outflow ports (12).

5. The continuous flow isoelectrofocusing apparatus according to claim 1, further comprising a vertical crosswall (17), substantially perpendicular to said vertical partitions, with outflow ports being provided on either side of said cross-wall.

6. A method of separating or purifying an amphoteric substance from an aqueous mixture, comprising:
 applying a sample containing the amphoteric substance to be separated or purified to the continuous flow apparatus of claim 1; and
 performing isoelectric focusing on the continuous flow apparatus to separate or purify the amphoteric substance.

7. The method according to claim 6, wherein a single upward flow of aqueous mixture is maintained.

8. The method according to claim 7, wherein said single flow is between 25 and 250 L per L per day.

9. The method according to claim 6, wherein the aqueous mixture to be separated comprises impurities in drinking water, alcoholic beverages and non-alcoholic beverages.

10. The method according to claim 6, wherein said substance is a polynucleotide, an amino acid, a peptide, a protein, including antigens and immunoglobulins, an enzyme, an antibiotic, an allergen, an alkaloid, or a component from a cell culture.

11. The method according to claim 6, wherein said substance is a substance expressed by or extracted from a microorganism, a terrestrial or marine animal or plant or parts or derivatives thereof.

* * * * *